United States Patent
Morris et al.

(10) Patent No.: US 9,060,860 B2
(45) Date of Patent: Jun. 23, 2015

(54) DEVICES AND METHODS FOR TRANSCATHETER HEART VALVE DELIVERY

(71) Applicants: St. Jude Medical, Inc., St. Paul, MN (US); St. Jude Medical, Cardiology Division, Inc., St. Paul, MN (US)

(72) Inventors: Benjamin E. Morris, Jeffersonville, IN (US); Eric E. Bielefeld, Floyds Knobs, IN (US); Gregory R. Furnish, Louisville, KY (US); Ralph Joseph Thomas, Champlin, MN (US); Khoi Le, Excelsior, MN (US); Bradley Charles Knippel, Lino Lakes, MN (US); Valerie J. Glazier, Eden Prairie, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 154 days.

(21) Appl. No.: 13/788,820

(22) Filed: Mar. 7, 2013

(65) Prior Publication Data
US 2013/0297011 A1 Nov. 7, 2013

Related U.S. Application Data

(60) Provisional application No. 61/642,875, filed on May 4, 2012, provisional application No. 61/665,527, filed on Jun. 28, 2012.

(51) Int. Cl.
*A61F 2/24* (2006.01)
*A61F 2/962* (2013.01)
*A61F 2/95* (2013.01)

(52) U.S. Cl.
CPC .............. *A61F 2/2436* (2013.01); *A61F 2/962* (2013.01); *A61F 2002/9517* (2013.01)

(58) Field of Classification Search
CPC ................ A61F 2/2427; A61F 2/2436; A61F 2002/95174; A61F 2002/9528; A61F 2002/9517; A61B 2017/00243

USPC .............. 623/1.11, 1.12, 2.11; 606/108, 139, 606/142, 143, 191, 200
See application file for complete search history.

(56) References Cited

U.S. PATENT DOCUMENTS

| | | | |
|---|---|---|---|
| 3,657,744 | A | 4/1972 | Ersek |
| 4,275,469 | A | 6/1981 | Gabbay |

(Continued)

FOREIGN PATENT DOCUMENTS

| | | |
|---|---|---|
| AU | 2011202175 B1 | 7/2011 |
| WO | 2012026965 A2 | 3/2012 |
| WO | 2012036741 A2 | 3/2012 |

OTHER PUBLICATIONS

International Search Report and Written Opinion for Application No. PCT/US2013/039407 dated Feb. 10, 2014.

*Primary Examiner* — Jonathan W Miles
(74) *Attorney, Agent, or Firm* — Lerner, David, Littenberg, Krumholz & Mentlik, LLP

(57) ABSTRACT

A delivery device for a collapsible prosthetic heart valve includes an operating handle and a catheter assembly. The operating handle may include a housing defining a movement space therein, a carriage assembly moveable in a longitudinal direction within the movement space, a deployment actuator coupled to the housing and rotatable relative to the housing, and a coupling assembly rotationally fixed to the deployment actuator. The catheter assembly may include a first shaft around which a compartment is defined and a distal sheath operatively connected to the carriage assembly. Movement of the carriage assembly in the longitudinal direction in the movement space may move the distal sheath between the closed condition and the open condition. The coupling assembly may have an engaged position in which rotation of the deployment actuator moves the carriage assembly, and a disengaged position in which rotation of the deployment actuator does not move the carriage assembly.

34 Claims, 10 Drawing Sheets

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,922,905 A | 5/1990 | Strecker |
| 5,391,172 A | 2/1995 | Williams et al. |
| 5,411,552 A | 5/1995 | Andersen et al. |
| 5,456,667 A | 10/1995 | Ham et al. |
| 5,480,423 A | 1/1996 | Ravenscroft et al. |
| 5,843,167 A | 12/1998 | Dwyer et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,736,845 B2 | 5/2004 | Marquez et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,326,236 B2 * | 2/2008 | Andreas et al. .............. 623/1.11 |
| 7,419,501 B2 * | 9/2008 | Chiu et al. ................... 623/1.12 |
| 7,993,384 B2 * | 8/2011 | Wu et al. ..................... 623/1.12 |
| 8,353,955 B2 | 1/2013 | Styrc et al. |
| 8,562,663 B2 * | 10/2013 | Mearns et al. ............... 623/1.12 |
| 8,568,475 B2 | 10/2013 | Nguyen et al. |
| 8,778,019 B2 * | 7/2014 | Knippel et al. ............... 623/2.11 |
| 8,790,386 B2 * | 7/2014 | Dwork ......................... 623/1.11 |
| 2003/0144725 A1 | 7/2003 | Lombardi |
| 2004/0186563 A1 | 9/2004 | Lobbi |
| 2005/0080476 A1 * | 4/2005 | Gunderson et al. .......... 623/1.11 |
| 2005/0240254 A1 * | 10/2005 | Austin ......................... 623/1.11 |
| 2011/0282425 A1 | 11/2011 | Dwork |
| 2011/0288626 A1 * | 11/2011 | Straubinger et al. ......... 623/1.12 |
| 2011/0295216 A1 * | 12/2011 | Miller .......................... 604/264 |
| 2012/0022635 A1 * | 1/2012 | Yamashita ................... 623/1.12 |
| 2012/0053574 A1 * | 3/2012 | Murray et al. ................ 606/1 |
| 2012/0078352 A1 * | 3/2012 | Wang et al. .................. 623/2.11 |
| 2012/0310332 A1 * | 12/2012 | Murray et al. ............... 623/2.11 |
| 2013/0030520 A1 * | 1/2013 | Lee et al. ..................... 623/2.11 |
| 2014/0067050 A1 * | 3/2014 | Costello et al. .............. 623/2.11 |
| 2014/0135909 A1 * | 5/2014 | Carr et al. .................... 623/2.11 |

* cited by examiner

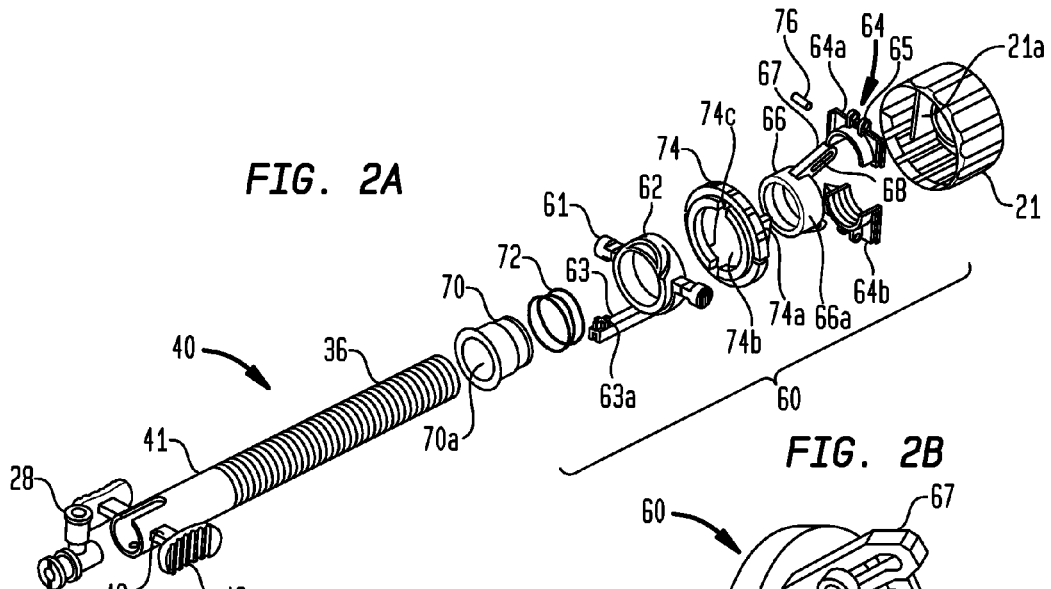
FIG. 2A
FIG. 2B
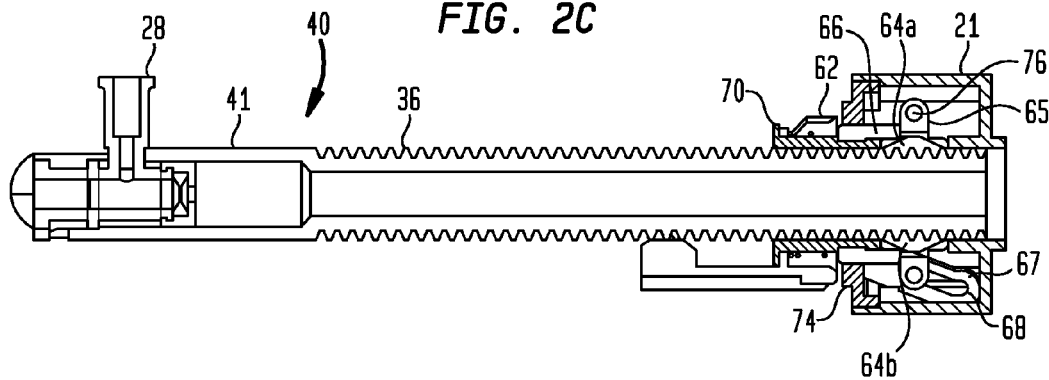
FIG. 2C
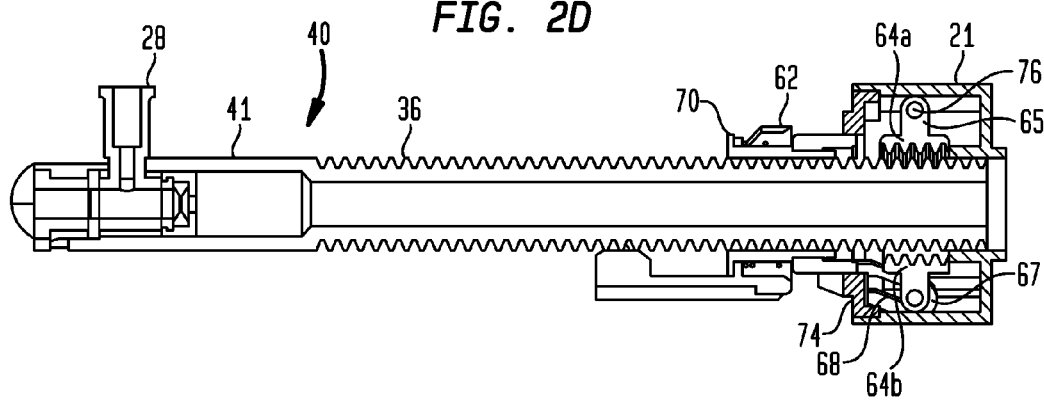
FIG. 2D

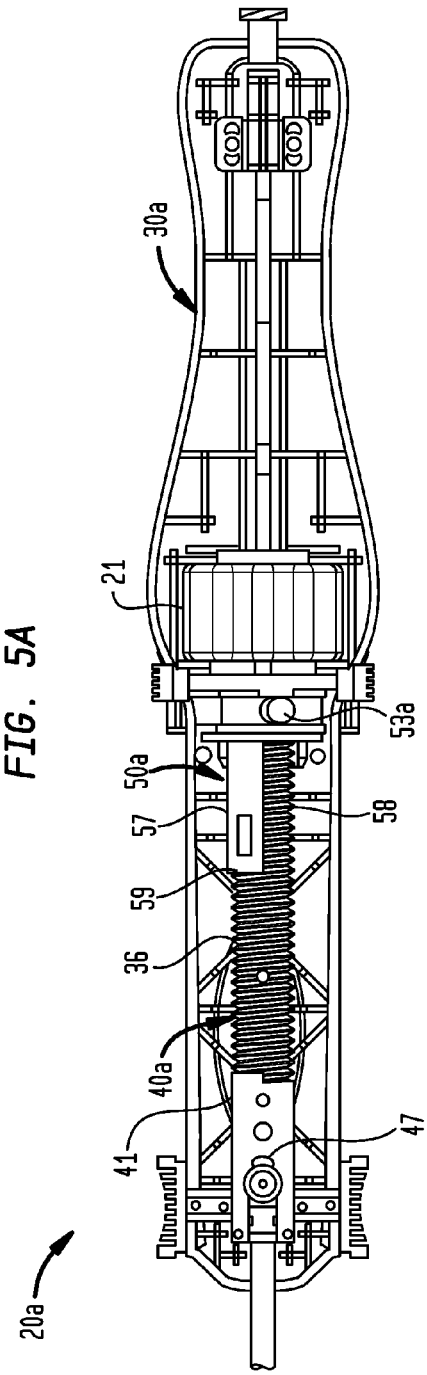
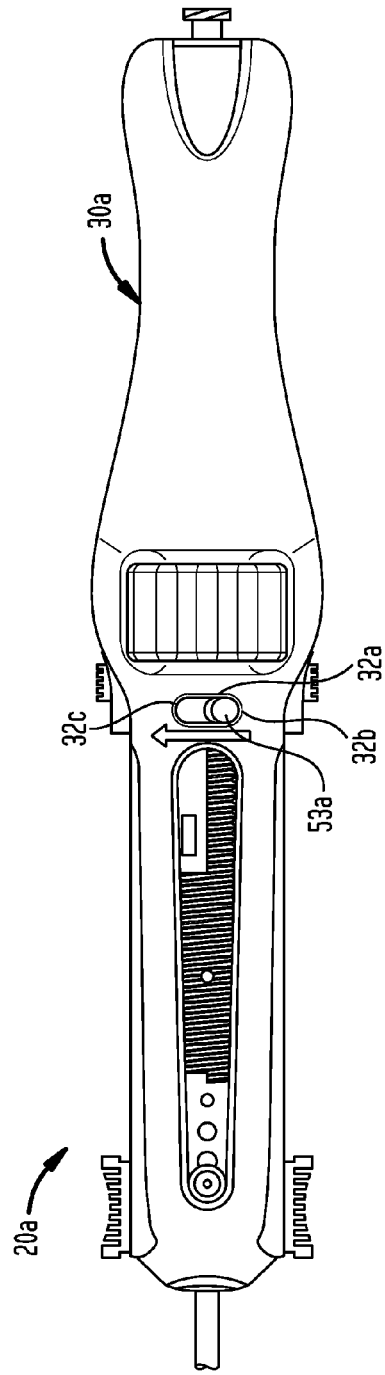
FIG. 5A
FIG. 5B

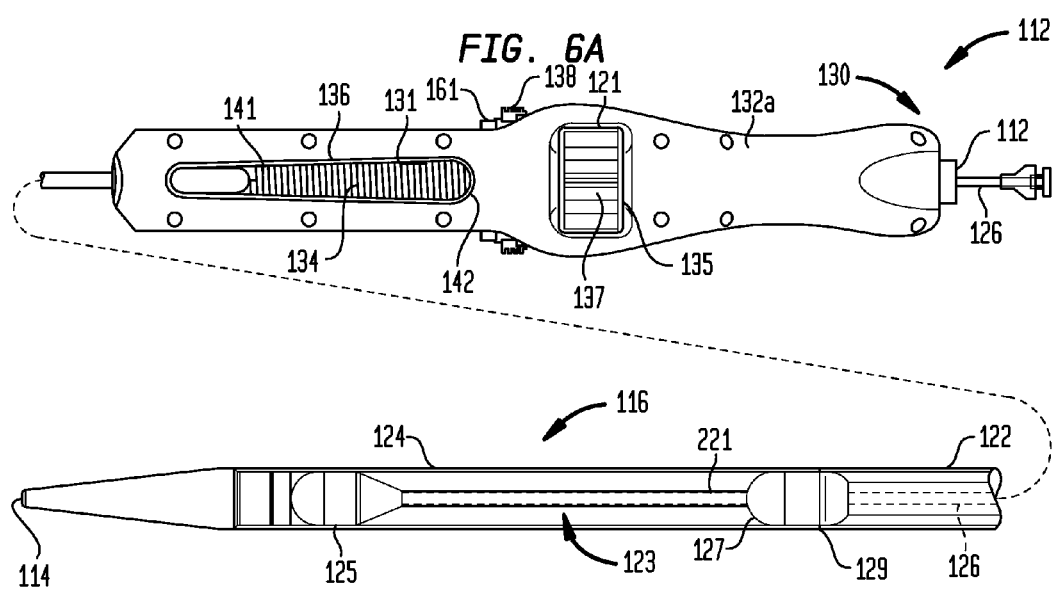
FIG. 6A
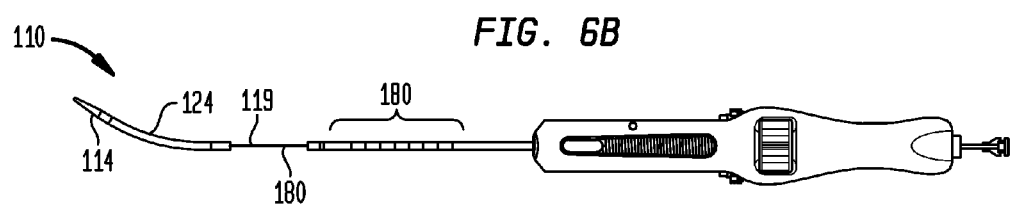
FIG. 6B
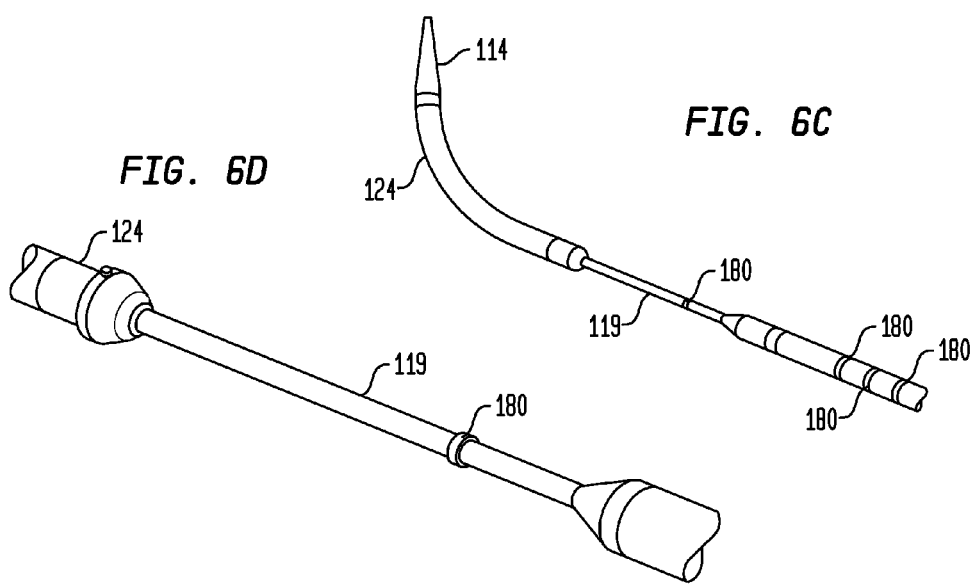
FIG. 6C
FIG. 6D

DEVICES AND METHODS FOR TRANSCATHETER HEART VALVE DELIVERY

CROSS-REFERENCE TO RELATED APPLICATION

This application claims the benefit of the filing date of U.S. Provisional Patent Application Nos. 61/642,875 filed May 4, 2012, and 61/665,527 filed Jun. 28, 2012, the disclosures of which are hereby incorporated herein by reference. The following commonly-owned applications are also hereby incorporated by reference herein: U.S. patent application Ser. No. 13/212,442, filed Aug. 18, 2011, and Ser. No. 13/234,782, filed Sep. 16, 2011.

BACKGROUND OF THE INVENTION

The present invention is related to prosthetic heart valve replacement, and more particularly to devices, systems, and methods for transapical and transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve, so that the valve can be repositioned while in a collapsed state. After the valve has been repositioned, the user can again release the valve.

Once a self-expanding valve has been fully deployed, it expands to a diameter larger than that of the sheath that previously contained the valve in the collapsed condition, making resheathing impossible, or difficult at best. In order for the user to be able to resheathe a partially-deployed valve, a portion of the valve must still be collapsed inside of the sheath.

Despite the various improvements that have been made to the collapsible prosthetic heart valve delivery process, conventional delivery devices, systems, and methods suffer from some shortcomings. For example, in conventional delivery devices for self-expanding valves, it is difficult to control how much of the valve remains in the sheath during a partial deployment, and the user may accidentally deploy the valve fully before verifying that the annulus end of the valve is in the optimal position in the patient's valve annulus, thereby taking away the opportunity to resheathe and reposition the valve.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

BRIEF SUMMARY OF THE INVENTION

Delivery devices for a collapsible prosthetic heart valve and methods of delivering a collapsible prosthetic heart valve using same are aspects of the invention. In addition, any device having one or more of the following features and used in the transcatheter delivery of a collapsible heart valve are the specific aspects of the invention.

A delivery device for a collapsible prosthetic heart valve includes an operating handle and a catheter assembly. The operating handle may include a housing defining a movement space therein, a carriage assembly moveable in a longitudinal direction within the movement space, a deployment actuator coupled to the housing and rotatable relative to the housing, and a coupling assembly rotationally fixed to the deployment actuator. The catheter assembly may include a first shaft around which a compartment is defined and a distal sheath operatively connected to the carriage assembly.

The coupling assembly may have an engaged position in which rotation of the deployment actuator moves the carriage assembly in the longitudinal direction, and a disengaged position in which rotation of the deployment actuator does not move the carriage assembly in the longitudinal direction. The first shaft may be operatively connected to the housing. The compartment may be adapted to receive the valve in an assembled condition. The distal sheath may be moveable between a closed condition covering the compartment and an open condition uncovering the compartment for deployment of the valve. Movement of the carriage assembly in the longitudinal direction in the movement space may move the distal sheath between the closed condition and the open condition.

The carriage assembly may include a threaded rod extending from a body of the carriage assembly and into threaded engagement with the coupling assembly. Rotation of the deployment actuator in a first direction may move the carriage assembly proximally in the longitudinal direction in the movement space, and rotation of the deployment actuator in a second direction opposite the first direction may move the carriage assembly distally in the longitudinal direction in the movement space. The coupling assembly may include a split nut having a plurality of threaded split nut portions. The split nut portions may each be linearly slideable away from one another and away from the threaded rod. The split nut may have an engaged position in which threads of the split nut portions are engaged with the threaded rod and a disengaged position in which the threads of the split nut portions do not engage the threaded rod.

The coupling assembly may include a ring coupled to the split nut portions. The ring may have cam surfaces. The split nut portions may be slideable along the cam surfaces when the split nut portions move between the engaged and disengaged positions. The deployment actuator may be a knob rotatable about a central axis that extends parallel to the longitudinal direction. The carriage assembly may include a toothed rack extending from a body of the carriage assembly and into threaded engagement with the coupling assembly. The deployment actuator may be a knob rotatable about a central axis that extends perpendicular to the longitudinal direction.

The operating handle may also include a resheathing lock having a lock position and a release position. The resheathing lock in the lock position may limit movement of the carriage assembly in the longitudinal direction to a stop position in the movement space. The resheathing lock in the release position may permit movement of the carriage assembly beyond the stop position. Movement of the carriage assembly to the stop position may move the distal sheath to a condition between the closed condition and the open condition so that the valve is not fully deployed. The compartment may have a first length and the stop position in the movement space corresponds to a travel distance of the carriage assembly. The travel distance may be less than the first length.

The collapsible prosthetic heart valve may have a second length, and the travel distance may be between about 80% and about 90% of the second length. The catheter assembly may also include an outer shaft attached to the distal sheath and operatively connected to the carriage assembly. The outer shaft may at least partially surround the first shaft. The operating handle may also include a mechanism adapted to move the first shaft proximally relative to the housing. The first shaft may be attached to the distal sheath and may be operatively connected to the carriage assembly. The catheter assembly may also include an outer shaft connecting the housing to the compartment and at least partially surrounding the first shaft.

The catheter assembly may also include an atraumatic tip having a lumen extending longitudinally therethrough and an insert located within the lumen. The first shaft may have an outwardly flared distal end that is fixed between a distal end of the insert and material forming the atraumatic tip. The insert may have a plurality of ribs. Each rib may extend continuously or discontinuously around a circumference of the insert. The atraumatic tip may have an outer surface that is concavely tapered in a longitudinal direction thereof.

A method of delivering a collapsible prosthetic heart valve in a patient includes providing a delivery device having a catheter assembly and an operating handle, the catheter assembly including a compartment adapted to receive the valve in an assembled condition. The operating handle may include a housing defining a movement space therein, a carriage assembly moveable in first and second longitudinal directions within the movement space, a deployment actuator coupled to the housing and rotatable relative to the housing, and a coupling assembly rotationally fixed to the deployment actuator.

The method may also include loading the valve into the compartment of the catheter assembly and covering the compartment and the valve with a distal sheath of the catheter assembly, inserting the catheter assembly into the patient so that the valve is positioned at a target location within the patient, partially deploying the valve by moving the carriage assembly of the operating handle in the first longitudinal direction along a first portion of the movement space, and fully deploying the valve by continuing movement of the carriage assembly in the first longitudinal direction along a second portion of the movement space.

The operating handle may also include a threaded rod extending from the carriage assembly and into threaded engagement with the coupling assembly. The deployment actuator may be longitudinally constrained relative to the housing. The partially deploying step may include rotating the deployment actuator. The coupling assembly may include a split nut having a plurality of threaded split nut portions. The split nut portions may each be linearly slideable away from one another and away from the threaded rod. The method may also include moving the split nut portions from a disengaged position in which threads of the split nut portions do not engage the threaded rod to an engaged position in which the threads of the split nut portions are engaged with the threaded rod.

The coupling assembly may include a ring coupled to the split nut portions. The ring may have cam surfaces. The step of moving the split nut portions may include sliding the split nut portions along the cam surfaces from the disengaged position to the engaged position. The deployment actuator may be a knob rotatable about a central axis that extends parallel to the first and second longitudinal directions. The operating handle may also include a toothed rack extending from the carriage assembly and into engagement with the coupling assembly. The deployment actuator may be longitudinally constrained relative to the housing. The partially deploying step may include rotating the deployment actuator. The deployment actuator may be a knob rotatable about a central axis that extends perpendicular to the first and second longitudinal directions.

The catheter assembly may also include a first shaft around which the compartment is defined and an outer shaft connecting the carriage assembly to the distal sheath and at least partially surrounding the first shaft. The first shaft may be fixedly connected to the housing. The distal sheath may be operatively connected to the carriage assembly. The steps of partially deploying the valve and fully deploying the valve may each include moving the outer shaft proximally relative to the housing. The catheter assembly may also include a first shaft around which the compartment is defined and an outer shaft connecting the housing to the compartment and at least partially surrounding the first shaft. The first shaft and the distal sheath may be operatively connected to the carriage assembly. The steps of partially deploying the valve and fully deploying the valve may each include moving the first shaft distally relative to the housing.

The operating handle may also include a resheathing lock having a lock position and a release position. The resheathing lock in the lock position may limit movement of the carriage assembly in the first longitudinal direction to a stop position in the movement space. The resheathing lock in the release position may permit movement of the carriage assembly in the first longitudinal direction beyond the stop position. The method may also include resheathing the valve by moving the carriage assembly in the second longitudinal direction opposite the first longitudinal direction. The target location may be the native aortic annulus of the patient. The inserting step may include inserting the distal sheath of the catheter assembly through a femoral artery of the patient. The inserting step may include inserting the distal sheath of the catheter assembly through the apex of the heart of the patient.

A delivery device for a collapsible prosthetic heart valve may include a first shaft around which a compartment is defined, an outer shaft surrounding at least a longitudinal portion of the first shaft, a distal sheath attached to one of the first shaft and the outer shaft and surrounding a longitudinal portion of the first shaft, and an atraumatic tip attached to a distal end of the first shaft. The first shaft may extend in a longitudinal direction and may have an outwardly flared portion at the distal end thereof. The compartment may be adapted to receive the valve in an assembled condition.

The outer shaft may be slidable relative to the first shaft in the longitudinal direction. The distal sheath may be moveable in the longitudinal direction between a closed condition covering the compartment and an open condition uncovering the compartment for deployment of the valve. The atraumatic tip may have a lumen extending longitudinally therethrough and an insert located within the lumen. The outwardly flared portion of the first shaft may be fixed between a distal end of the insert and material forming the atraumatic tip. The insert may have a plurality of ribs. Each rib may extend continuously or discontinuously around a circumference of the insert. The atraumatic tip may have an outer surface that is concavely tapered in the longitudinal direction.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIG. 2A is an exploded perspective view of the deployment actuator assembly of FIG. 1C;

FIG. 2B is an enlarged perspective view of a portion of the deployment actuator assembly of FIG. 1C;

FIG. 2C is a longitudinal cross-section of the deployment actuator assembly of FIG. 1C, with the deployment actuator shown in threaded engagement with the carriage assembly;

FIG. 2D is a longitudinal cross-section of the deployment actuator assembly of FIG. 1C, with the deployment actuator shown disengaged from the threads of the carriage assembly;

FIG. 5A is a top view of another embodiment of an operating handle for a transfemoral delivery device for a collapsible prosthetic heart valve, shown with a portion of the housing removed;

FIG. 5B is a top view of the operating handle of FIG. 5A, shown with the entire housing;

FIG. 6A is a top perspective view of an operating handle for a transapical delivery device for a collapsible prosthetic heart valve, shown with a top view of the distal portion of a transapical catheter assembly;

FIG. 6B is a top perspective view of a delivery device including the operating handle of FIG. 6A, shown with the compartment unsheathed;

FIGS. 6C and 6D are enlarged perspective views of portions of the delivery device of FIG. 6B;

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user.

Figure 1A:
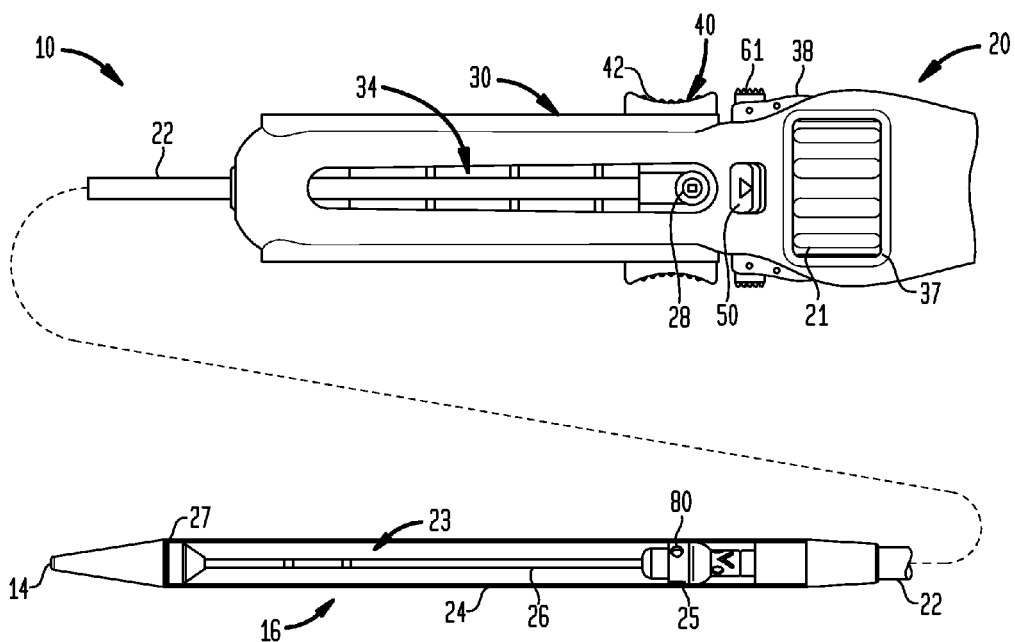
FIG. 1A is a top plan view of a portion of an operating handle for a transfemoral delivery device for a collapsible prosthetic heart valve, shown with a partial longitudinal cross-section of the distal portion of a transfemoral catheter assembly.
Figure 1B:
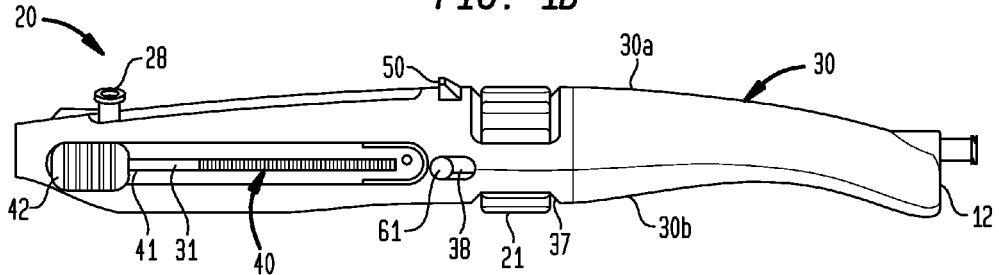
FIG. 1B is a side view of the handle of FIG. 1A.
Figure 1C:
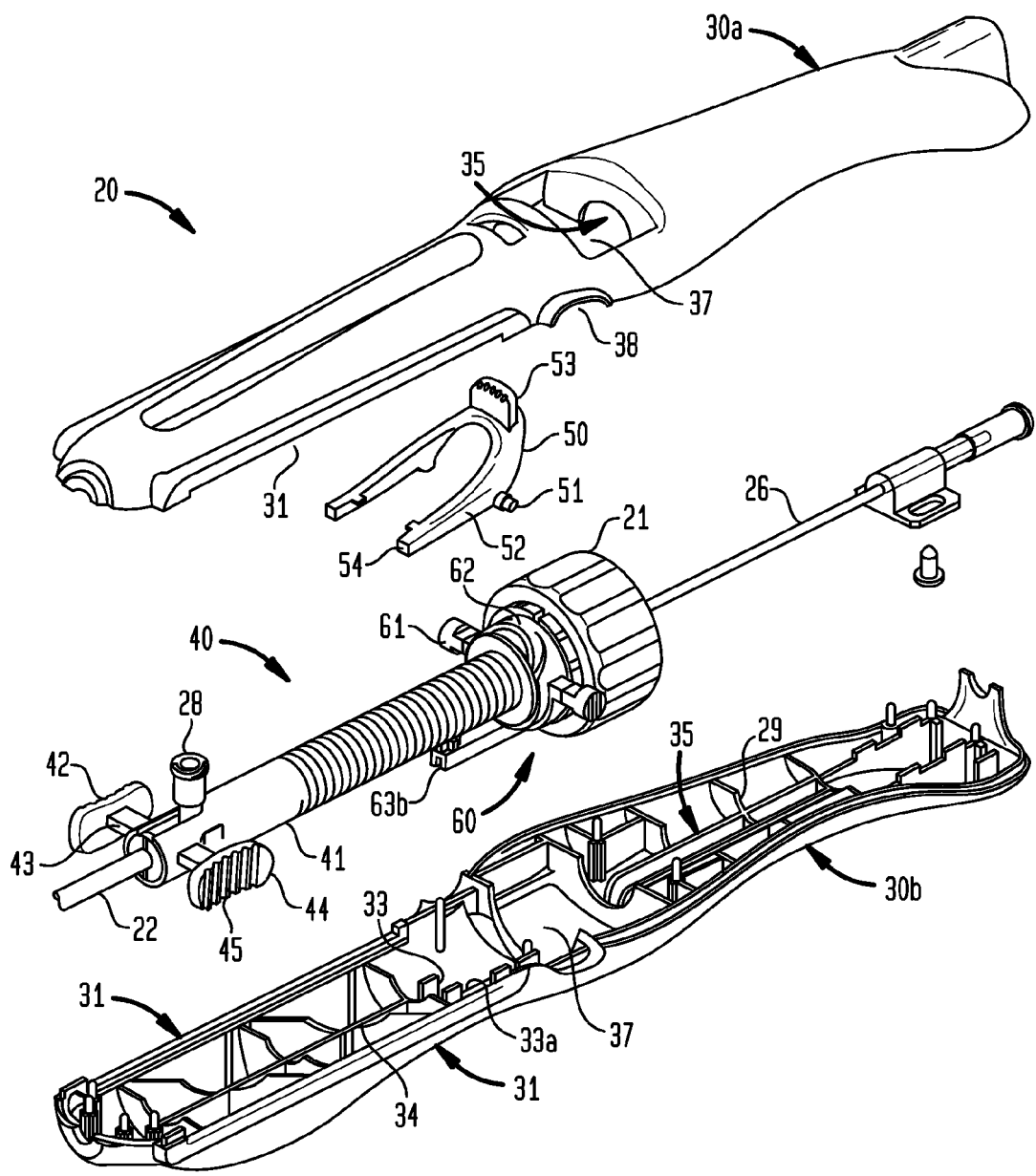
FIG. 1C is an exploded perspective view of the handle of FIG. 1A.

Referring now to FIGS. 1A-1C to illustrate the structure and function of the present invention, an exemplary transfemoral delivery device 10 for a collapsible prosthetic heart valve (or other types of self-expanding collapsible stents) has a catheter assembly 16 for delivering the heart valve to and deploying the heart valve at a target location, and an operating handle 20 for controlling deployment of the valve from the catheter assembly. The delivery device 10 extends from a proximal end 12 (FIG. 1B) to an atraumatic tip 14 at the distal end of catheter assembly 16. The catheter assembly 16 is adapted to receive a collapsible prosthetic heart valve (not shown) in a compartment 23 defined around an inner shaft 26 and covered by a distal sheath 24.

The inner shaft 26 may extend through the operating handle 20 to the atraumatic tip 14 of the delivery device, and includes a retainer 25 affixed thereto at a spaced distance from tip 14 and adapted to hold a collapsible prosthetic valve in the compartment 23. The inner shaft 26 may be made of a flexible material such as braided polyimide or polyetheretherketone (PEEK), for example. Using a material such as PEEK may improve the resistance of the inner shaft 26 to kinking while the catheter assembly 16 is tracking through the vasculature of a patient. The retainer 25 may have recesses 80 therein that are adapted to hold corresponding retention members of the valve.

The distal sheath 24 surrounds the inner shaft 26 and is slidable relative to the inner shaft such that it can selectively cover or uncover the compartment 23. The distal sheath 24 is affixed at its proximal end to an outer shaft 22, the proximal end of which is connected to the operating handle 20 in a manner to be described. The distal end 27 of the distal sheath 24 abuts the atraumatic tip 14 when the distal sheath is fully covering the compartment 23, and is spaced apart from the atraumatic tip when the compartment 23 is at least partially uncovered.

The operating handle 20 is adapted to control deployment of a prosthetic valve located in the compartment 23 by permitting a user to selectively slide the outer shaft 22 proximally or distally relative to the inner shaft 26, thereby respectively uncovering or covering the compartment with the distal sheath 24. The outer shaft 22 may be made of a flexible material such as nylon 11 or nylon 12, and it may have a round braid construction (i.e., round cross-section fibers braided together) or flat braid construction (i.e., rectangular cross-section fibers braided together), for example. The proximal end of the inner shaft 26 may be connected in substantially fixed relationship to an outer housing 30 of the operating handle 20 (the longitudinal position of the inner shaft relative to the housing may be movable in some embodiments, for example, as described below with reference to FIGS. 11A and 11B), and the proximal end of the outer shaft 22 is affixed to a carriage assembly 40 that is slidable along a longitudinal axis of the handle housing, such that a user can selectively slide the outer shaft relative to the inner shaft by sliding the carriage assembly relative to the housing. A hemostasis valve 28 includes an internal gasket adapted to create a seal between the inner shaft 26 and the proximal end of the outer shaft 22.

The handle housing 30 includes a top portion 30a and a bottom portion 30b. The top and bottom portions 30a and 30b may be individual pieces joined to one another as shown in FIG. 1C. Collectively, the top and bottom portions 30a and 30b define an elongated space 34 in the housing 30 in which the carriage assembly 40 may travel. The elongated space 34 preferably permits the carriage assembly 40 to travel a distance that is at least as long as the anticipated length of the prosthetic valve to be delivered (e.g., at least about 50 mm), such that the distal sheath 24 can be fully retracted from around the prosthetic valve. A pair of slots 31 may be formed on opposite sides of the housing 30, contiguous with the elongated space 34. The length of the slots 31, minus the width of the carriage grip shafts 43 (described below), determines the maximum distance that the carriage assembly 40 can travel within the space 34.

The carriage assembly 40 has a body portion 41 with a threaded rod 36 extending proximally therefrom along the longitudinal axis of the housing 30. A series of ribs 29 in the handle housing 30 collectively define an enlarged bore 35 (FIG. 1C) that is sized to freely and slidingly receive a threaded rod 36. The enlarged bore 35 has an inner diameter slightly larger than the outer diameter of the threaded rod 36. The threaded rod 36 preferably is longer than the anticipated maximum travel distance of the carriage assembly 40 within the elongated space 34 (e.g., at least about 50 mm), such that the threaded rod 36 does not fully disengage from the deployment actuator 21 (described below) during sheathing or resheathing of the prosthetic valve.

The carriage assembly 40 further includes a pair of carriage grips 42 each attached to the body portion 41 by a respective carriage grip shaft 43. Although the carriage assembly 40 is shown in FIGS. 1A and 1C as having two carriage grips 42, that need not be the case. For example, the embodiment shown in FIG. 6A has a single carriage grip. As shown in FIG. 1C, the lateral sides 44 of the carriage grips 42 may include a plurality of parallel ridges 45 to facilitate grasping and moving of the carriage grips.

The handle housing 30 further defines a pocket 37 that extends through the top portion 30a and bottom portion 30b for receiving a deployment actuator 21. Deployment actuator 21 is internally threaded for selective engagement with the threaded rod 36. The pocket 37 is sized and shaped to receive the deployment actuator 21 with minimal clearance, such that the location of the deployment actuator remains substantially fixed relative to the housing 30 as it is rotated about the threaded rod 36. That is, when the deployment actuator 21 is in threaded engagement with the threaded rod 36, rotation of the deployment actuator in one direction (either clockwise or counterclockwise depending on the orientation of the threads on the threaded rod) causes the threaded rod to move proximally within the bore 35, at the same time pulling the body portion 41 of the carriage assembly 40 proximally through the elongated space 34. Similarly, when the deployment actuator 21 is in threaded engagement with the threaded rod 36, rotation of the deployment actuator in the opposite direction causes the threaded rod to move distally within the bore 35, at the same time pushing the body portion 41 of the carriage assembly 40 distally through the elongated space 34.

The deployment actuator 21 may be selectively placed in threaded engagement with the threaded rod 36 by a coupling assembly 60, the details of which are shown in FIGS. 2A-2D. The coupling assembly 60 may include a split nut 64 mounted within the deployment actuator 21 through an open side thereof. The split nut 64 has first and second nut portions 64a and 64b that are internally threaded to mate with the threaded rod 36. Each nut portion 64a and 64b has a pair of spaced tabs projecting therefrom, with each tab having an aperture 65 sized to receive a pin 76.

A nut ramp 66 may be mounted within the deployment actuator 21 adjacent the split nut 64. The nut ramp 66 has an annular body 66a with a pair of cam arms 67 projecting distally therefrom and slidably positioned between the spaced tabs on respective nut portions 64a and 64b. Each cam arm 67 has an elongated cam slot 68 sized to slidably receive the pin 76 therein.

A retention ring 74 may be press fit into the open side of the deployment actuator 21. A plurality of ribs on the outer periphery of the retention ring 74 may mate with a plurality of recesses formed on the inner surface of the deployment actuator 21 to prevent the retention ring from rotating relative to the deployment actuator. The retention ring 74 may include a pair of spaced flanges 74a that cooperate with similar spaced flanges formed on the interior of the deployment actuator 21 to sandwich the generally rectangular outer periphery of the split nut 64 in an assembled position. A large central aperture 74b in the retention ring 74 is sized to slidably receive the annular body 66a of the nut ramp 66 therethrough. The retention ring 74 further includes a pair of diametrically opposed slots 74c that are sized and positioned to receive the cam arms 67 of the nut ramp 66 as the annular body 66a thereof travels through the aperture 74b in the retention ring.

A ring 62 may be positioned adjacent the retention ring 74 and may be coupled to the nut ramp 66 by a flanged fastening ring 70 that fits through the ring 62 and snaps into the nut ramp with an interference fit. The connection between the fastening ring 70 and the nut ramp 66 is such that the ring 62 has some freedom of movement between the annular body 66a of the nut ramp and the flange of the fastening ring. An aperture 70a extending longitudinally through the fastening ring 70 has a diameter that is larger than the diameter of the threaded rod 36 so that the threaded rod can slide smoothly and freely therethrough. A compression spring 72, the purpose of which will be described below, may be mounted in the annular space between the fastening ring 70 and the ring 62 and may be constrained longitudinally between the annular body 66a of the nut ramp 66 and an annular flange formed on the ring 62.

A pair of buttons 61 positioned on opposite lateral sides of the ring 62 may be slidably received in longitudinal openings 38 formed on opposite lateral sides of the housing 30. Movement of the buttons 61 to a proximal position in the openings 38 will cause the ring 62 and, hence, the nut ramp 66 to move proximally relative to the split nut 64, and movement of the buttons 61 to a distal position in the openings 38 will cause the ring 62 and the nut ring 66 to move distally relative to the split nut.

The ring 62 further includes an arm 63 that extends distally from an outer periphery of the ring. The arm 63 is sized to reside between a pair of posts 33 that project upwardly from the housing portion 30b. The free end of the arm 63 includes a pair of nubs 63a that project therefrom in opposite lateral directions. When the buttons 61 are moved to a distalmost position in the opening 31, the nubs 63a will be positioned on the distal side of the posts 33, locking the ring 32 in this position. When the buttons 61 are moved to a proximalmost position in the openings 38, the nubs 63a will be positioned on the proximal side of the posts 33, locking the ring in this position. As the buttons 61 are moved between the proximalmost and distalmost positions, the nubs 63a will deflect the posts 33 slightly outward as they move between the posts. The engagement of a rib 33a extending longitudinally in the housing portion 30b in a longitudinal slot 63b on the back of the arm 63 maintains the alignment of the ring 62 as it slides between the proximalmost and distalmost positions.

The first and second nut portions 64a and 64b have freedom of motion to slide in a substantially perpendicular direction towards or away from the threaded rod 36, but they are constrained from longitudinal movement relative to the threaded rod by the sandwiching effect of the inner flanges of the deployment actuator 21 and the retention ring flanges 74a. Thus, in the assembly described above, the cam slots 68 are adapted to translate movement of the nut ramp 66 along the longitudinal axis into lateral movement of the first and second nut portions 64a and 64b towards or away from the threaded rod 36.

For example, when the buttons 61 are moved to the proximal ends of the respective openings 38, the pins 76 will be disposed at the distal ends of the cam slots 68, which are located closest to the threaded rod 36 in a direction perpendicular to the longitudinal axis. In this position, the nut portions 64a and 64b will be in threaded engagement with the threaded rod 36. When the buttons 61 are moved to the distal ends of the respective openings 38, the pins 76 will be disposed at the proximal ends of the cam slots 68, which are located farthest from the threaded rod 36 in the direction perpendicular to the longitudinal axis. In this position, the nut portions 64a and 64b will be disengaged from the threaded rod 36. Therefore, when a user slides the buttons 61 proximally, rotation of the deployment actuator 21 translates the threaded rod 36, and when the user slides the buttons distally, the deployment actuator becomes decoupled from the threaded rod.

When the user slides the buttons 61 proximally to move the nut portions 64a and 64b toward the threaded rod 36, interference between the threads on the nut portions and the threads on the threaded rod may prevent complete threaded engagement between the split nut 64 and the threaded rod. Nonetheless, the ring 62 will move to its proximalmost position so that the nubs 63a snap into place on the proximal side of the posts 33. With the aforementioned interference preventing the nut portions 64a and 64b from continuing into full threaded engagement with the threaded rod 36, and thus preventing the nut ramp 66 from further movement proximally, the last portion of the movement of the ring 62 in the proximal direction will cause the spring 72 to compress. This compression will add an extra lateral force to the nut ramp 66. Accordingly, as the deployment actuator 21 is rotated, the threads of the nut portions 64a and 64b will properly align with the threads of threaded rod 36 and the biasing force exerted by the spring 72 on the nut ramp 66 will assure that the nut portions become fully engaged with the threaded rod.

The ability of the coupling assembly 60 to translate rotation of the deployment actuator 21 into translation of the carriage assembly 40 relative to the housing 30 may provide the user with the ability to carefully control movement of the carriage assembly both proximally within the space 34 during a valve deployment operation, and distally within the space 34 during a resheathing operation, as described more fully below. The ability of the coupling assembly 60 to decouple the deployment actuator 21 from the carriage assembly 40 so that the carriage assembly can freely move longitudinally relative to the housing 30 enables gross movement of the carriage assembly proximally or distally within the space 34 without the mechanical advantage provided by the deployment actuator. Such movement is not easily controllable, but rather is subject to the "touch and feel" of the user.

Referring now to FIGS. 3A-3D, the carriage assembly may include a resheathing lock adapted to limit the longitudinal movement of the carriage assembly proximally within the handle housing 30, thereby preventing the user from completing the deployment of a prosthetic valve when unintended. One embodiment of a resheathing lock may include a control member 50 that is pivotable relative to the housing 30 between a lock position (shown in FIG. 3A) and a release position (shown in FIG. 3D).

Figure 3A:
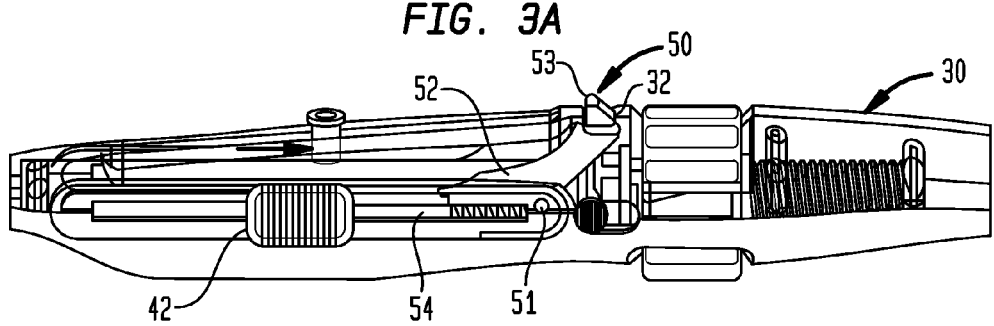
FIG. 3A is a partially transparent side perspective view of a portion of the operating handle of FIG. 1A, showing the carriage assembly in an intermediate position.
Figure 3B:
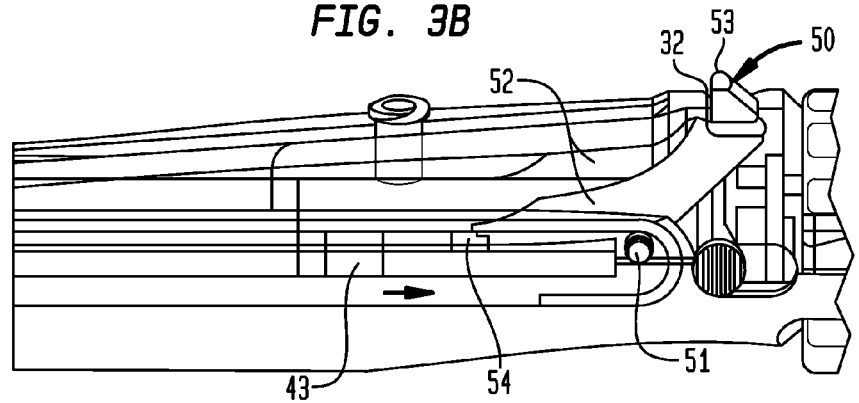
FIG. 3B is an enlarged partially transparent side perspective view of a portion of the operating handle of FIG. 1A, showing the carriage assembly in another intermediate position.
Figure 3C:
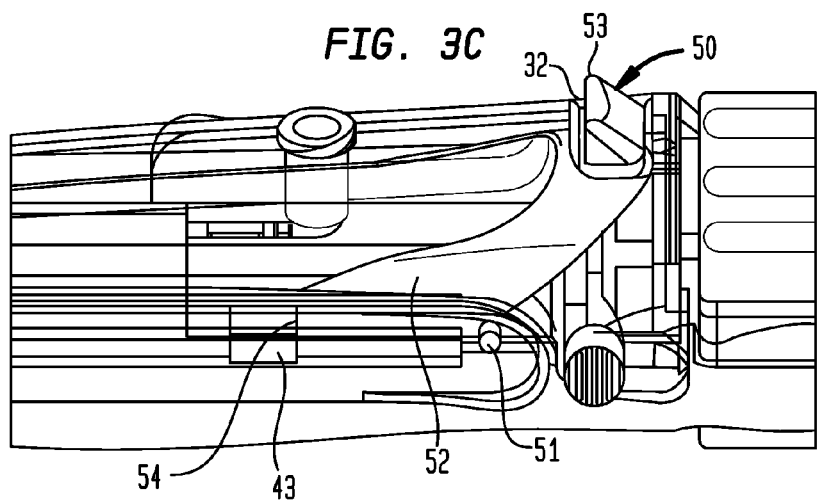
FIG. 3C is an enlarged partially transparent side perspective view of a portion of the operating handle of FIG. 1A, showing the carriage assembly in contact with the deployment lock.

The control member 50 includes a pair of spaced arms 52 that extend distally into the space 34 in the housing 30. Each arm 52 terminates in a notch 54 that is adapted to interfere with a respective carriage grip shaft 43 when the control member 50 is in the lock position, thereby preventing the carriage assembly 40 from continued proximal movement, as shown in FIG. 3C. A pin 51 projects laterally from each arm (only one such pin 51 is shown in the drawings) and is pivotally engaged in respective apertures 39 formed on opposite sides of the housing 30. The pins 51 are not positioned in the center of arms 52, but rather are positioned much closer to the proximal end of the control member 50. As a result, a much greater weight of the control member 50 resides between the pins 51 and the notches 54 than between the pins 51 and the proximal end of the control member, such that the weight differential biases the control member to the lock position.

Figure 3D:
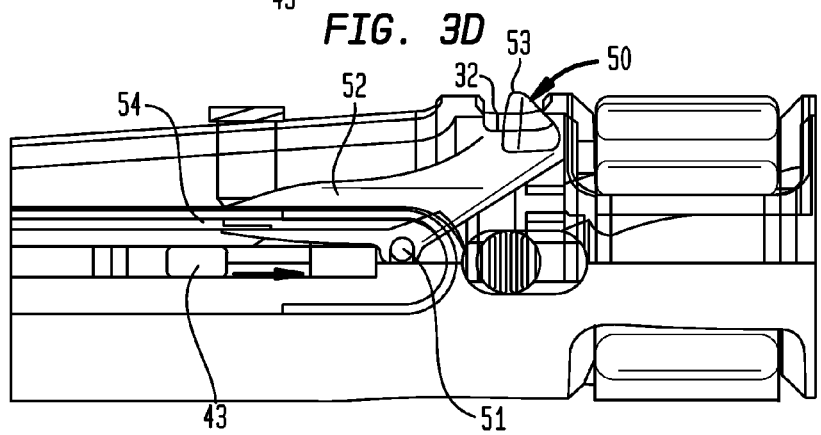
FIG. 3D is a partially transparent side view of a portion of the operating handle of FIG. 1A, showing the deployment lock in an actuated position.

With the control member 50 in its lock position (shown in FIG. 3A), a button 53 on the proximal end of the control member projects through an opening 32 in the housing 30, where it is available to be pressed by the user. Depressing the button 53 overcomes the weight-based biasing force and pivots the control member 50 about the pins 51, causing the notched end of each arm 52 to move up and out of engagement with the respective carriage grip shaft 43. This action thus frees the carriage assembly 40 for further proximal movement relative to the housing 30, as shown in FIG. 3D, thereby permitting full deployment of a prosthetic valve from the catheter assembly 16.

The initial distance that the carriage assembly 40 can travel before being limited by the control member 50 may depend on the structure of the particular prosthetic valve to be deployed. Preferably, the initial travel distance of the carriage assembly 40 is about 3 mm to about 5 mm less than the crimped valve length. Alternatively, the initial travel distance of the carriage assembly 40 may be about 40 mm to about 45 mm, which is about 80% to about 90% of the length of an exemplary 50 mm valve. The initial distance that the carriage assembly 40 can travel may be determined as a percentage of the length of the prosthetic valve and/or the compartment 23, including, for example, 50%, 60%, 70%, 75%, 85%, or 95%.

Figure 4A:
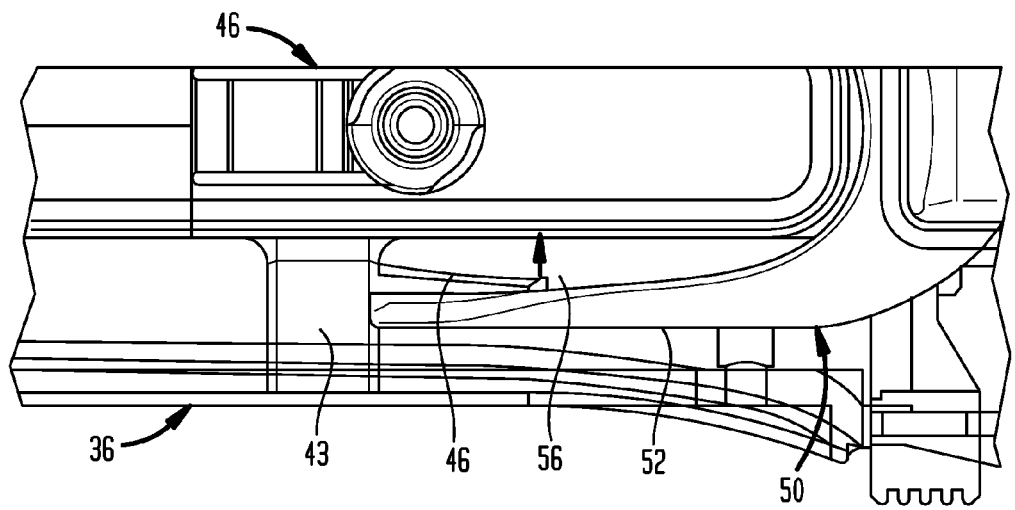
FIG. 4A is a partially transparent top view of a portion of the operating handle of FIG. 1A, showing the arms of the deployment lock contacting the reset lever.
Figure 4B:
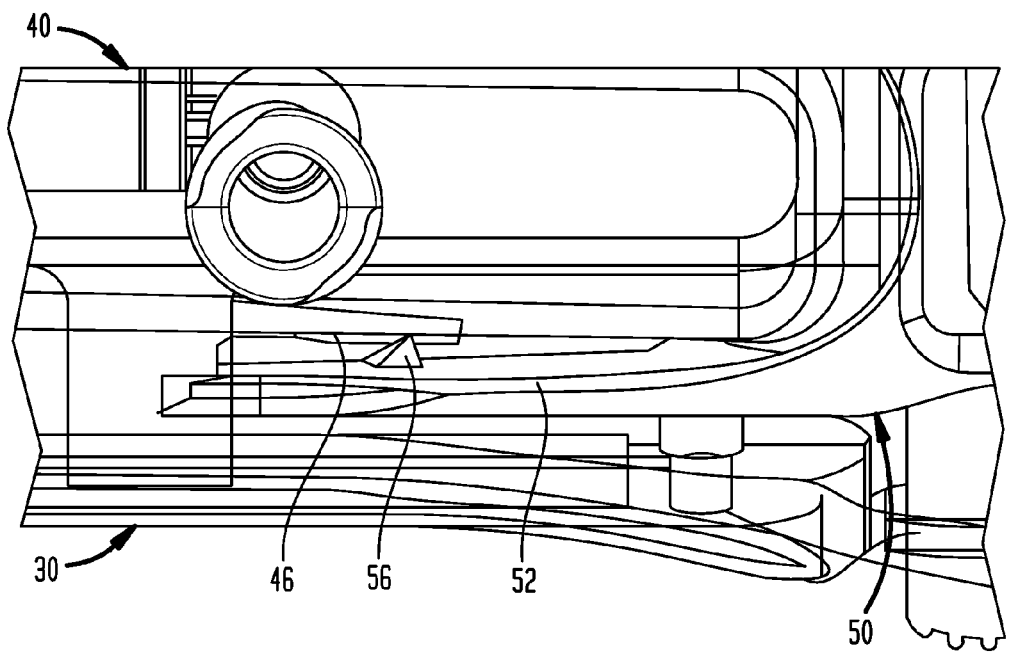
FIG. 4B is a partially transparent top perspective view of a portion of the operating handle of FIG. 1A, showing the arms of the deployment lock overlying the reset lever.

Referring now to FIGS. 4A and 4B, each arm 52 of the control member 50 may also include one or more protrusions 56 that project laterally towards the longitudinal axis of the housing 30, and each carriage grip shaft 43 may include a reset lever 46 extending proximally therefrom. During proximal movement of the carriage assembly 40, as the carriage grip shafts 43 approach the ends of the arms 52, the reset levers 46 will contact the protrusions 56 and will be deflected laterally inward towards the longitudinal axis of the housing 30. The reset levers 46 will continue to be deflected laterally inward as the carriage assembly 40 continues to move proximally until the notches 54 at the ends of the arms 52 engage the carriage grip shafts 43.

At this juncture, to continue deployment, the button 53 may be depressed to pivot the ends of the arms 52 up and away from the carriage grip shafts 43. As the arms 52 pivot upwardly, the protrusions 56 will also move upwardly until they are positioned above the reset levers 46, which then return to their straight or undeflected condition. The protrusions 56 will thereafter rest on the upper surfaces of the reset levers 46, thereby holding the control member 50 in the release position, even after the button 53 has been released by the user. The fact that the control member 50 remains in the release position even after the button 53 has been released frees the user to again operate the deployment actuator 21, thus enabling one-handed operation of the device 10.

When the carriage assembly 40 is moved distally to resheathe the compartment 23 with distal sheath 24, the protrusions 56 will ride along the top of reset levers 46, with the control member 50 in the release position, until the carriage grip shafts 43 have moved just distally of the notches 54. At this point, the protrusions 56 will clear the reset levers 46 and the weight of the arms 52 will bias control member 50 back to the lock position.

The operation of the present invention to deploy a prosthetic valve will now be described. To load the delivery device 10 with a collapsible prosthetic valve, the user may place the buttons 61 in the distalmost position within the openings 38 to disengage the split nut 64 from the threaded rod 36. The carriage grips 42 may then be slid proximally relative to the slots 31 to move the carriage assembly 40 proximally and thereby retract the distal sheath 24 and expose the compartment 23. During this retraction, the button 53 may be depressed to place the control member 50 in its release position to enable the carriage assembly 40 to move fully to its proximalmost position and thereby fully expose the compartment 23. A compressed or crimped valve may then be loaded around the inner shaft 26, and the proximal end of the valve may be coupled to the retainer 25. The carriage grips may then be slid in the opposite or distal direction relative to the slots 31 to move the carriage assembly 40 distally and cover the compartment 23 with the distal sheath 24 to hold the valve in the compressed state. The buttons 61 may then be placed in the starting condition of the delivery device 10. In this starting condition, the handle 20 will be in an initial state with the carriage assembly 40 at its distalmost position within the handle housing 30, the control member 50 of the resheathing lock will be in its lock position to prevent full deployment, and the buttons 61 will each be at the proximalmost position within the respective openings 38, such that the deployment actuator 21 is threadedly engaged with the threaded rod 36.

To use the operating handle 20 to deploy a prosthetic valve that has been loaded into the compartment 23 and covered by the distal sheath 24, the user may rotate the deployment actuator 21, causing the carriage assembly 40 to slide proximally within the elongated space 34 in the housing 30. Because the distal sheath 24 is affixed to the outer shaft 22, which in turn is affixed to the carriage assembly 40, and because the inner shaft 26 is fixed to the housing 30, sliding the carriage assembly proximally relative to the housing will retract the distal sheath proximally from the compartment 23, thereby exposing and initiating deployment of the valve located therein.

It will be appreciated that the user may initiate the deployment process without use of the deployment actuator 21 by simply sliding the buttons 61 of the coupling assembly 60 distally, thereby decoupling the split nut 64 from the threaded rod 36, and pulling the carriage assembly 40 proximally within the housing 30. Such action may require significant pulling force in order to overcome the frictional forces acting on the outer shaft 22 and the distal sheath 24.

For that reason, the use of the deployment actuator 21 to begin retracting the distal sheath 24 is preferred since such use provides the user with a mechanical advantage to overcome the aforementioned frictional forces, thereby providing the user with much greater control of the deployment process.

After the distal sheath 24 has been partially retracted from the compartment 23 and a portion of the prosthetic valve has been exposed, the frictional forces acting between the valve and the distal sheath may be greatly reduced. At this point, the user may continue the deployment process with or without use of the deployment actuator 21. If the user prefers to continue the deployment process without use of the deployment actuator 21, the user can slide the buttons 61 of the coupling assembly 60 distally to disengage the split nut 64 from the threaded rod 36 and can pull the carriage assembly 40 proximally within the housing 30 by exerting a pulling force on carriage grips 42. Although the user will not have a mechanical advantage without using the deployment actuator 21 to move the carriage assembly 40 proximally, continuing the deployment process while the deployment actuator is decoupled from the carriage assembly may allow such process to be completed more quickly.

In any event, since the control member 50 of the resheathing lock is in the lock position, movement of the carriage assembly 40 proximally may continue only until the carriage grip shafts 43 contact the notches 54 at the ends of the arms 52. At this point, the distal sheath 24 will not be fully withdrawn from the compartment 23, and the prosthetic valve will not be fully deployed.

When the deployment procedure has reached this juncture, the user can evaluate the position of the valve relative to the patient's aortic annulus and may be able to determine whether the valve is functioning properly. If repositioning or removal is desired, with the buttons 61 positioned to engage the split nut 64 with the threaded rod 36, the user may resheathe the valve by rotating the deployment actuator 21 in the direction opposite that used for deployment. Such rotation will cause the threaded rod 36 to progress distally through the deployment actuator 21 until the carriage assembly 40 has reached the starting position shown in FIG. 1B, thereby recollapsing the expanded part of the valve as the distal sheath 24 is moved distally over the compartment 23 and the partially deployed valve. With the valve resheathed, the user can reposition the delivery device 10 and can commence the deployment procedure once again or can simply remove the valve from the patient.

It will be appreciated that the user may partially or fully resheathe the valve without use of the deployment actuator 21 by simply sliding the buttons 61 of the coupling assembly 60 distally, thereby decoupling the deployment actuator from the carriage assembly 40, and pushing the carriage assembly distally within the housing 30. Such action may require significant pushing force in order to overcome the frictional forces acting on the outer shaft 22 and the distal sheath 24, as well as the resilient forces which expand the stent portion of the valve. For that reason, a user may choose to use the deployment actuator 21 to replace the distal sheath 24 over the compartment 23 since such use provides the user with a mechanical advantage to overcome the aforementioned forces.

Once the proper positioning of the valve relative to the aortic annulus has been assured, the user may complete the deployment process. To do so, the user may depress the button 53 of the control member 50 of the resheathing lock, thereby causing the control member to pivot from the lock position to the release position and the arms 52 to pivot upward out of the path of the carriage grip shafts 43 so that the carriage assembly 40 is free to continue its movement proximally. The user can continue to slide the carriage assembly 40 proximally to complete the deployment of the valve by rotating the deployment actuator 21 or by sliding the buttons 61 of the coupling assembly 60 distally to decouple the deployment actuator from the carriage assembly 40, and pulling the carriage assembly proximally within the housing 30. When the valve has been completely unsheathed, the stent portion of the valve self-expands and disengages from the retainer 25, thereby releasing the valve from the catheter assembly 16.

Referring now to FIG. 5A, an operating handle 20a is shown having an alternate resheathing lock design than that shown in FIGS. 1A through 4B. The resheathing lock of the operating handle 20a includes a control member 50a that is rotatable between first and second positions relative to the housing 30a and the carriage assembly 40. The control member 50a includes a generally cylindrical body 57 disposed between the housing 30a and the threaded rod 36, such that the threaded rod extends through a generally cylindrical opening extending through the control member along the longitudinal direction of the housing 30.

The cylindrical body 57 of the control member 50a has a distal end 59 and a slot 58 extending proximally from the distal end in the longitudinal direction of the housing 30. The distal end 59 is adapted to interfere with a protrusion 47 on the body 41 of the carriage assembly 40 when the control member 50a is in the lock position shown in FIGS. 5A and 5B, thereby preventing the carriage assembly from continued proximal movement.

With the control member 50a in its lock position, a button 53a on the proximal end of the control member projects through an opening 32a in the housing 30, where it is available to be moved by the user. Sliding the button 53a from the lock position adjacent a first end 32b of the opening 32a to a second opposite end 32c of the opening slightly rotates the control member 50a about the threaded rod 36, causing the slot 58 to rotate into alignment with the protrusion 47. As the slot 58 is sized to receive the protrusion 47 therein, this action frees the carriage assembly 40 for further proximal movement relative to the housing 30, thereby permitting full deployment of a prosthetic valve from the catheter assembly 16.

Referring now to FIG. 6A, an exemplary transapical delivery device 110 for a collapsible prosthetic heart valve (or other types of self-expanding collapsible stents) has a catheter assembly 116 for delivering the heart valve to and deploying the heart valve at a target location, and an operating handle 120 for controlling deployment of the valve from the catheter assembly. The delivery device 110 extends from a proximal end 112 to an atraumatic tip 114 at the distal end of the catheter assembly 116. The atraumatic tip 114 may be formed from or may include a radiopaque material to enable the tip to be visible under fluoroscopy during a deployment procedure. The catheter assembly 116 is adapted to receive a collapsible prosthetic heart valve (not shown) in a compartment 123 defined around a tubular support shaft 119 and covered by a distal sheath 124.

The support shaft 119 extends between a pair of spaced retainers 125 and 127 affixed thereto and defining the ends of the compartment 123. A collapsible prosthetic valve may be assembled around the support shaft 119 and between the retainers 125 and 127 in the compartment 123.

The distal sheath 124 surrounds the support shaft 119 and is slidable relative to the support shaft such that it can selectively cover or uncover the compartment 123. The distal sheath 124 is affixed at its distal end to the atraumatic tip 114, and its proximal end 129 terminates at or near the retainer 127 when the distal sheath is fully covering the compartment 123, as shown in FIG. 6A. The proximal end 129 of the distal sheath 124 is spaced apart from the retainer 127 when the compartment 123 is at least partially uncovered.

The delivery device further includes an outer shaft 122, the proximal end of which is fixedly connected to the operating handle 120, and the distal end of which terminates at or near the retainer 127, and preferably abuts the proximal end 129 of the distal sheath 124 when the distal sheath is in the proximalmost position. An inner shaft 126 extends through the operating handle 120 and the support shaft 119 to the atraumatic tip 114. The connection of the distal sheath 124 to the atraumatic tip 114 thus enables the inner shaft 126 to control the movement of the distal sheath both proximally and distally.

The operating handle 120 is adapted to control deployment of a prosthetic valve located in the compartment 123 by permitting a user to selectively slide the inner shaft 126 and the attached distal sheath 124 distally or proximally relative to the support shaft 119, thereby respectively uncovering or covering the compartment with the distal sheath. The proximal end of the outer shaft 122 is connected in substantially fixed relationship to an outer housing 130 of the operating handle 120, and a location near the proximal end of the inner shaft 126 is connected to a carriage assembly (similar to the carriage assembly 40 described above) that is slidable along a longitudinal axis of the handle housing, such that a user can selectively slide the inner shaft relative to the outer shaft by sliding the carriage assembly relative to the housing. As shown in FIG. 6A, the inner shaft 126 may extend through the carriage assembly, and the proximal end of the inner shaft may extend through the housing 130 beyond the proximal end 112 thereof. A hemostasis valve 128 attached to the proximal end of the inner shaft 126 may permit removal of air from the device 110 through the inner shaft before deployment of the valve.

The handle housing 130 includes a top portion 130a and a bottom portion (not shown in the figures). The top portion 130a and bottom portion may be similar to the top and bottom portion 30a and 30b described above. Collectively, the top portion 130a and bottom portion define an elongated space 134 in the housing 130 in which the carriage assembly may travel.

The housing 130 also includes a slot 131 contiguous with the elongated space 134. The length of the slot 131, minus the width of the carriage grip shaft (not visible in the figures, but similar to the carriage grip shafts 43 described above) that attaches the carriage grip 142 to the body portion 141 of the carriage assembly, determines the maximum distance that the carriage assembly can travel within the space 134. Although only one slot 131 is shown in FIG. 6A, a second slot 131 and a second carriage grip 142 may be provided on the opposite side of the housing 130, similar to the configuration shown in FIG. 1A. As shown, the slot 131 extends through the top portion 130a of the housing 130. An enlarged bore 135 defined by the housing 130 is sized to freely and slidingly receive a threaded rod 136 that extends proximally from the body portion 141 of the carriage assembly, as described below.

The device 110 may include a coupling assembly to convert rotational motion of a deployment actuator 121 into linear motion of the carriage assembly. The coupling assembly may be configured in much the same manner as the coupling assembly 60 described above with reference to FIGS. 1C through 2D, and the pair of buttons 161 engaged in respective openings 138 can have a structure and function similar to those of the buttons 61 of the device 10 described above.

The deployment actuator 121 may be located within a pocket 137 extending transversely through the housing 130, and it may selectively be placed in threaded engagement with the threaded rod 136. When the deployment actuator 121 is in threaded engagement with the threaded rod 136, rotation of the deployment actuator in one direction (either clockwise or counterclockwise depending on the orientation of the threads on the threaded rod) causes the threaded rod to move proximally within the bore 135, at the same time pulling the carriage assembly proximally through the elongated space 134. Similarly, when the deployment actuator 121 is in threaded engagement with the threaded rod 136, rotation of the deployment actuator in the opposite direction causes the threaded rod to move distally within the bore 135, at the same time pushing the body portion 141 of the carriage assembly distally through the elongated space 134. The deployment actuator 121 may be selectively placed in threaded engagement with the threaded rod 136 by a coupling assembly similar to the coupling assembly 60 described above with respect to the device 10.

The operating handle 120 may also include a resheathing lock mechanism for preventing the user from accidentally completing the deployment of a valve located in the compartment 123. Although such a resheathing lock is not shown in FIG. 6A, the resheathing lock may be similar to those described above with reference to FIGS. 1A through 5B. As with device 10, such a sheath lock may limit the longitudinal movement of the carriage assembly within the handle housing 130.

Referring to FIGS. 6B-6D, the delivery device 110 may include measurement markings 180 thereon to assist the user in determining the location or depth of portions of the device with respect to the aortic annulus or the apex of the heart. One or more of the markings 180 also may be located on the distal sheath 124, so that the user can determine how far the distal sheath has moved during deployment of a valve relative to its initial position. One or more of the markings 180 may be located on the support shaft 119 at the anticipated location of the leaflets of the prosthetic aortic valve, so that the user can know where the leaflets are relative to the native aortic annulus during deployment of the valve.

Each of the measurement markings 180 may include a material selected from the group consisting of a polymer, gold, platinum, nitinol, and combinations thereof, or one or more other metallic or polymer materials, and such markings may be radiopaque, i.e., the markings may be visible to the user under fluoroscopy.

The operation of the operating handle 120 to deploy a prosthetic valve from the compartment 123 is similar to the operation of the operating handle 20 of the device 10 described above. The user can rotate the deployment actuator 121 to slide the carriage assembly distally within the elongated space 134 in the housing 130, which thereby pushes the distal sheath 124 distally relative to the compartment 123 and exposes and initiates deployment of the valve located therein.

After movement of the distal sheath 124 has partially revealed the compartment 123, the user may continue the deployment process by continuing to rotate the deployment actuator 121, or the user may continue the deployment process without use of the deployment actuator by sliding the buttons 161 of the coupling assembly distally, thereby decoupling the deployment actuator from the threaded rod, and pushing the carriage assembly distally within the housing 130. Similar to the deployment process described above with reference to the operating handle 20, completing the deployment process while the carriage assembly is decoupled from the deployment actuator 121 may allow such process to be completed more quickly.

Although not shown in the figures, it will be appreciated that the device 110 may include a resheathing lock with a control member and reset levers similar to the control member 50 and the reset levers 46 described above in connection with the control handle 20; a resheathing lock with a slotted control member, protrusion, and actuator button similar to the control member 50a, the protrusion 47, and the actuator button 53a described above in connection with the control handle 20a; or other structures for limiting the movement of the carriage assembly within the handle housing. However, rather than limiting the movement of the carriage assembly proximally within the handle housing, the resheathing lock of the device 110 will limit the movement of the carriage assembly distally within the housing to prevent the user from completing the deployment of a prosthetic valve unintentionally.

If the user desires to resheathe and reposition the valve or remove the valve from the patient before full deployment, the user can do so by rotating the deployment actuator 121 in the direction opposite that used for deployment until the carriage assembly reaches the starting position (with the carriage grip 142 in its proximalmost position in the slot 131), thereby recollapsing the expanded part of the valve as the distal sheath 124 is moved proximally over the compartment 123 and the partially deployed valve. With the valve resheathed, the user can reposition the delivery device 110 and commence the deployment procedure once again or can remove the valve from the patient.

Once the proper positioning of the valve has been assured, the deployment operation may be completed by continuing to slide the carriage assembly distally by rotating the deployment actuator 121 or by sliding the buttons 161 of the coupling assembly distally to decouple the deployment actuator from the threaded rod, and pushing the carriage assembly distally within the housing 130 until the valve is fully deployed.

Referring now to FIGS. 7A-11B, an exemplary transfemoral delivery device 210 is a variation of the delivery device 10 described above, with a similar function of deploying a collapsible prosthetic heart valve (or other types of self-expanding collapsible stents). However, some of the components of the delivery device 210 have different structures for accomplishing similar functions as the delivery device 10.

Figure 7A:
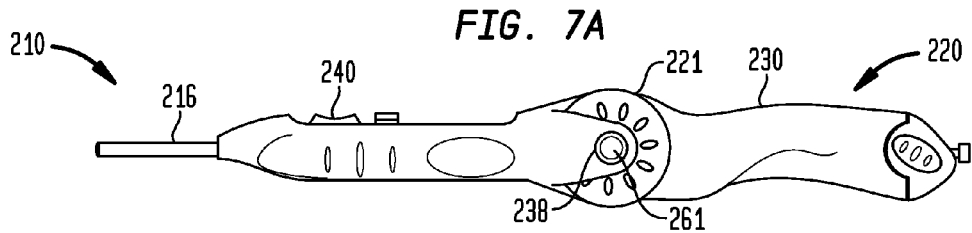
FIG. 7A is a side view of another embodiment of an operating handle for a transfemoral delivery device for a collapsible prosthetic heart valve.
Figure 7B:
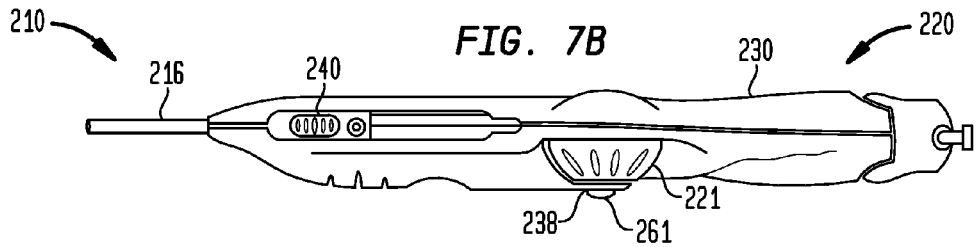
FIG. 7B is a top plan view of the handle of FIG. 7A.
Figure 7C:
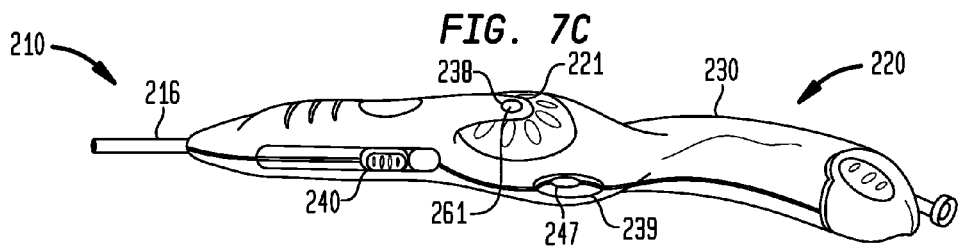
FIG. 7C is a bottom perspective view of the handle of FIG. 7A.

Referring to FIGS. 7A-7C, the device 210 includes a catheter assembly 216 adapted to receive a collapsible prosthetic heart valve in a compartment defined around an inner shaft 226 (FIG. 11A) and covered by a distal sheath 224, and an operating handle 220 for controlling deployment of the valve. The proximal end of the inner shaft 226 is operatively coupled in a fixed manner to an outer housing 230 of the operating handle 220.

Figure 8A:
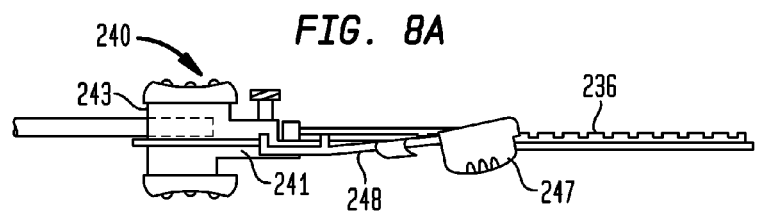
FIG. 8A is a side view of the rack assembly of the operating handle of FIG. 7A.
Figure 8B:
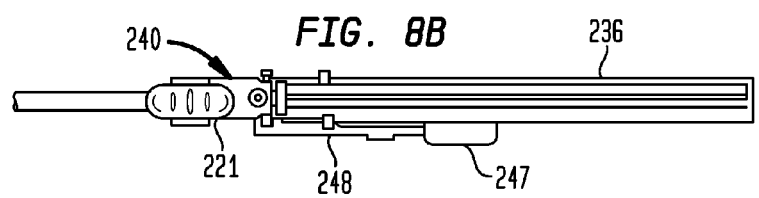
FIG. 8B is a top view of the rack assembly of FIG. 8A.

The device 210 includes a deployment actuator 221 that may be selectively engaged with a carriage assembly 240 (FIG. 8A). When the deployment actuator 221 is engaged with the carriage assembly 240 and is rotated in a first direction relative to the housing 230, the rotational motion is translated to linear motion of the carriage assembly either proximally or distally relative to the housing, and when the deployment actuator is rotated in an opposite direction relative to the housing, the carriage assembly moves linearly in an opposite direction relative to the housing. When the deployment actuator 221 is disengaged from the carriage assembly 240, the carriage assembly can be manually moved by a user along the longitudinal axis of the housing 230 without any resulting movement of the deployment actuator 221.

Figure 8C:
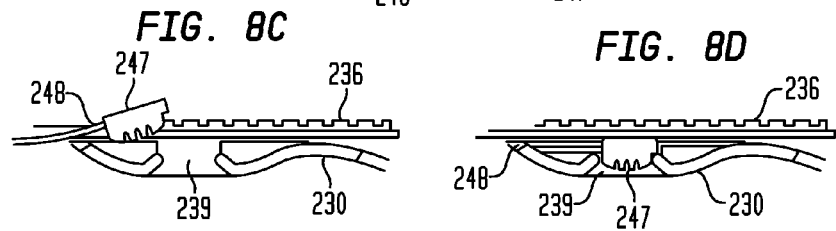
FIG. 8C is a longitudinal cross-section showing a portion of the rack assembly of FIG. 8A with a portion of the handle of FIG. 7A.

As can be seen in FIGS. 8A-8D, the carriage assembly 240 is similar to the carriage assembly 40 described above, except that the carriage assembly 240 has a toothed rack 236 adapted to be engaged with the deployment actuator 221, instead of a threaded rod. Rather than having the carriage grip shafts 243 contact another component to provide a resheathing lock feature, the carriage assembly 240 includes a plug 247 coupled to the body 241 by a leaf spring 248 and adapted to engage with an aperture 239 in the housing 230 to provide a resheathing lock feature. When the carriage assembly 240 is in its initial distalmost position shown in FIGS. 7A and 7B, the plug 247 lies against an inner surface of the housing 230 as shown in FIG. 8C, such that the leaf spring 248 is in a bent condition as shown in FIG. 8A. The leaf spring is displaced from its rest position and therefore causes the plug 247 to exert a force against the inner surface of the housing.

Figure 8D:
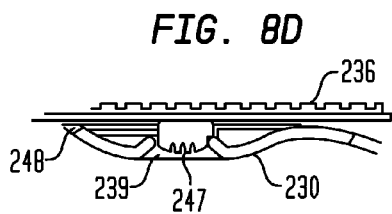
FIG. 8D is a longitudinal cross-section showing a portion of the rack assembly of FIG. 8A engaged with an opening in a portion of the handle of FIG. 7A.

During deployment of the valve, when the carriage assembly 240 is moved proximally and reaches the desired deployment lock position (e.g., a distance from the initial position of approximately 80% of the length of the valve as described above), the plug 247 reaches the aperture 239 as shown in FIG. 8D, and the stored energy in the leaf spring 248 forces the plug into the aperture as the leaf spring attempts to return to a straight or rest condition. When the user desires to continue deployment of the valve, the user can depress the plug 247 to remove it from the aperture 239 while simultaneously rotating the deployment actuator 221, thereby moving the carriage assembly 240 proximally and the plug proximally beyond the aperture.

Referring now to FIGS. 9A through 10B, the deployment actuator 221 may be selectively placed in engagement with the toothed rack 236 by a coupling assembly 260. The deployment actuator 221 has a hub portion 262 that includes an annular series of elongated fingers 262a that are separated by a plurality of deep channels 262b. A pinion gear 266 has a hub portion 264 that confronts the hub portion 262 of the deployment actuator 221. The hub portion 264 has an annular series of elongated fingers 264a that are separated by a plurality of deep channels 264b. The fingers 264a are sized and spaced to fit within the channels 262b and the fingers 262a are sized and spaced to fit within the channels 264b when the hub portion 262 is fully engaged with the hub portion 264. The hub portion 262 of the deployment actuator 221 is kept in engagement with the hub portion 264 of the gear 266 by a compression spring 268 positioned between the gear and an inner surface of the housing 230. The gear 266 also has a plurality of teeth 270 on its outer periphery that are adapted to engage the teeth of the rack 236.

Figure 9A:
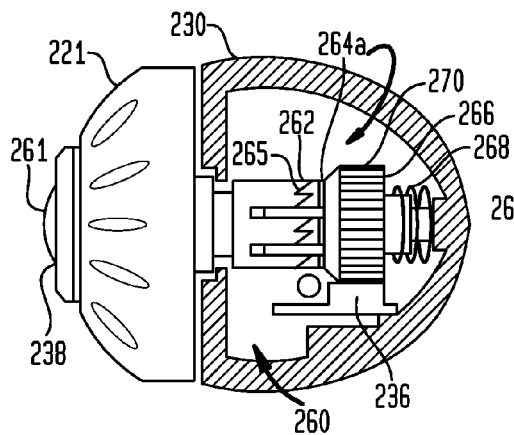
FIG. 9A is a side view of the motion transfer assembly of the operating handle of FIG. 7A, shown in partial cross-section with the pinion engaged with the rack.
Figure 9B:
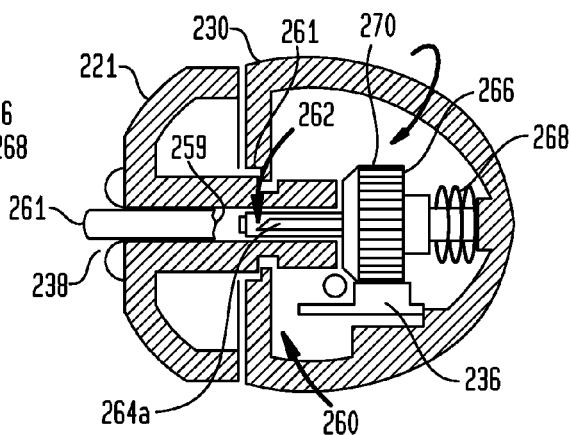
FIG. 9B is a cross-sectional view of the motion transfer assembly and rack of FIG. 9A.

FIGS. 9A and 9B show the deployment actuator 221 engaged with the toothed rack 236 through the gear 266. When the gear 266 is in the engaged position shown in FIGS. 9A and 9B, the fingers 264a of the gear are rotationally aligned with and engaged in the corresponding channels 262b in the hub portion 262 of the deployment actuator 221, so that rotation of the deployment actuator effects rotation of the gear. When the gear 266 is in this engaged position, the teeth 270 of the gear are engaged with the rack 236, so that rotation of the gear effects linear movement of the rack. Therefore, when the gear 266 is in the engaged position, the rotation of the deployment actuator 221 is transferred into linear movement of the rack 236, and, in turn, linear movement of the entire carriage assembly 240.

Figure 10A:
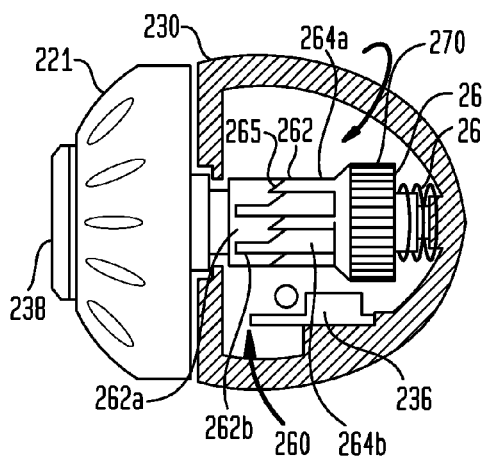
FIG. 10A is a side view of the motion transfer assembly of the operating handle of FIG. 7A, shown in partial cross-section with the pinion disengaged from the rack.
Figure 10B:
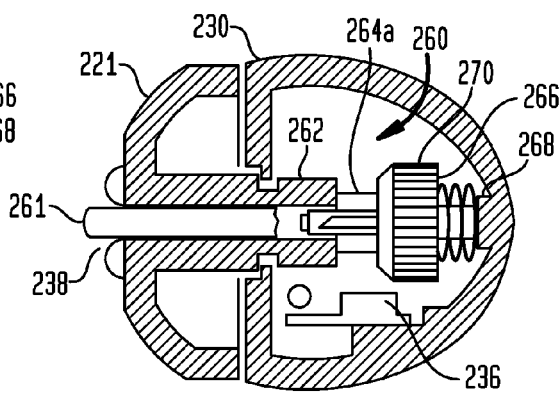
FIG. 10B is a cross-sectional view of the motion transfer assembly and rack of FIG. 10A.

FIGS. 10A and 10B show the deployment actuator 221 disengaged from the toothed rack 236. When the gear 266 is in the disengaged position shown in FIGS. 10A and 10B, the fingers 264a of the gear are rotationally aligned with and engaged in corresponding shallow notches 265 at the ends of fingers 262a of the deployment actuator 221. Such engagement still causes rotation of the deployment actuator 221 to result in rotation of the gear 266. However, when the gear 266 is in this disengaged position, the teeth 270 of the gear are disengaged from the rack 236, so that rotation of the gear is not transferred to the rack. Moreover, the rack 236 is free for sliding movement longitudinally in the housing 230. Therefore, when the gear 266 is in the disengaged position, the user can manually slide the carriage assembly 240 proximally or distally without interference or resistance from the deployment actuator 221.

To move the gear 266 from the engaged position shown in FIGS. 9A and 9B to the disengaged position shown in FIGS. 10A and 10B, the user can depress and release a button 261 mounted in an aperture 238 through the deployment actuator 221. The button 261 has an outer end exposed for actuation by the user, and an inner end having a plurality of notches 259 that confront the hub portion 264 of the gear 266. The button 261 is constrained so as to be able to move linearly along the axis of the aperture 238, but not be able to rotate about the axis of the aperture with respect to the deployment actuator 221.

When the user depresses the button 261, the notches 259 at the inner end of the button are brought into contact with the ends of the fingers 264a of the gear 266. Continued depressing of the button 261 displaces the gear 266 laterally until the gear teeth 270 are moved out of engagement with the rack 236. The fingers 264a each have an angled tip 267 that is not aligned with the trough at the bottom of the corresponding notch 259. Rather, as the button 261 is depressed, each angled tip 267 contacts the angled sidewall of a notch 259. The spring 268 forces the angled tips 267 into the troughs of the notches 259, thereby rotating the gear 266 slightly so that the angled tips and the troughs of the notches are rotationally aligned.

Following the rotation of the gear 266, the angled tips 267 of the fingers 264a will also be aligned with the shallow notches 265 of the deployment actuator 221. Therefore, when the user releases the button 261, the spring 268 forces the angled tips 267 of the fingers 264a into the shallow notches 265 at the ends of the fingers 262a. Since the fingers 264a are engaged in the shallow notches 265 rather than in the deep channels 262b, the gear teeth 270 remain disengaged from the rack 236, as shown in FIGS. 10A and 10B.

To move the gear 266 from the disengaged position shown in FIGS. 10A and 10B back to the engaged position shown in FIGS. 9A and 9B, the user can depress and release the button 261 again. When the user depresses the button 261, the notches 259 at the inner end of the button are brought into contact with the ends of fingers 264a of the gear 266. This contact pushes the tips 267 of fingers 264a out of engagement with the shallow notches 265. Once again, the angled tip 267 on each of the fingers 264a will not be aligned with the trough at the bottom of the corresponding notch 259. Rather, as the button 261 is depressed, each angled tip 267 contacts the angled sidewall of a notch 259. The spring 268 forces the angled tips 267 into the troughs of the notches 259, thereby rotating the gear 266 slightly so that the angled tips and the troughs of the notches are rotationally aligned.

After the rotation of gear 266, the angled tips 267 of the fingers 264a will also be aligned with the deep channels 262b of the deployment actuator 221. As a result, when the user releases the button 261, the spring 268 forces the angled tips 267 of the fingers 264a into the deep channels 262b. Since the fingers 264a are engaged in the deep channels 262b rather than in the shallow notches 265, the gear 266 is able to move laterally until the teeth 270 of the gear engage with the rack 236, as shown in FIGS. 9A and 9B.

Figure 11A:
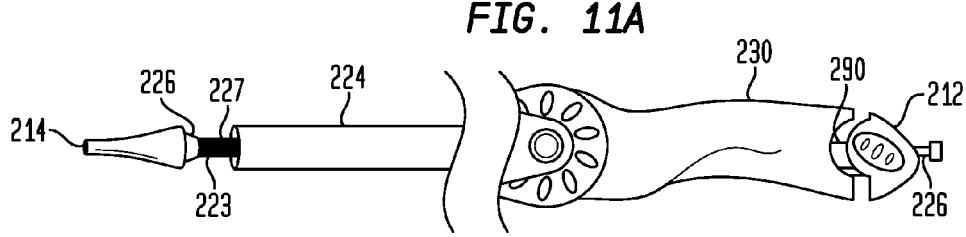
FIG. 11A is a side view showing a portion of the handle of FIG. 7A with the proximal end of the rack assembly engaged with the housing, and a side elevation of the distal portion of a transfemoral catheter assembly in a first condition.
Figure 11B:
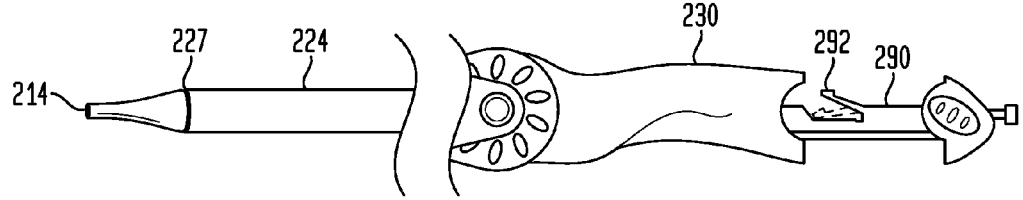
FIG. 11B is a side view showing a portion of the handle of FIG. 7A with the proximal end of the rack assembly disengaged from the housing, and a side elevation of the distal portion of the transfemoral catheter assembly in a second condition.

Referring now to FIGS. 11A and 11B, the device 210 may include a detachable proximal tip 212 to permit the user to more easily resheathe the compartment 223 after deployment of the valve, preferably before the device is removed from the patient. The detachable proximal tip 212 may include a shaft member 290 and a resilient contact arm 292 extending from the shaft member. The contact arm 292 may attach the proximal tip 212 to the housing 230 with a bayonet-type connection. After deployment of the valve has been completed, when the distal sheath 224 has uncovered the compartment 223 that previously stored the valve, the proximal end of the rack 236 may contact the shaft member 290 and push the proximal tip 212 out of the housing 230. This can serve as a signal to the user that deployment of the valve has been completed.

To easily and quickly resheathe the compartment 223 for the purpose of removing the device 210 from the patient, the user may pull the proximal tip 212 proximally. The inner shaft 226 is affixed to the proximal tip 212 such that pulling the proximal tip 212 proximally also pulls the inner shaft proximally. Since the distal sheath 224 is connected to the carriage assembly 240 that cannot move further proximally relative to the housing 230 following full deployment, sliding the inner shaft 226 proximally relative to the housing will resheathe the compartment 223 until the atraumatic tip 214 contacts the distal end 227 of the distal sheath. With the compartment 223 closed, the device 210 may be removed from the patient without the need to further operate the deployment actuator 221, disengage the gear 266 from the rack 236 or perform any other time-consuming operation.

The operating handles described herein may be provided with a deployment locking mechanism. Such a deployment locking mechanism may prevent the accidental initiation of deployment by fixing the carriage assembly to the handle housing while the lock is in a locked position. Such a deployment lock may have a structure similar to the deployment locks shown and described in co-pending U.S. patent application Ser. No. 13/212,442, filed Aug. 18, 2011.

Figure 12A:
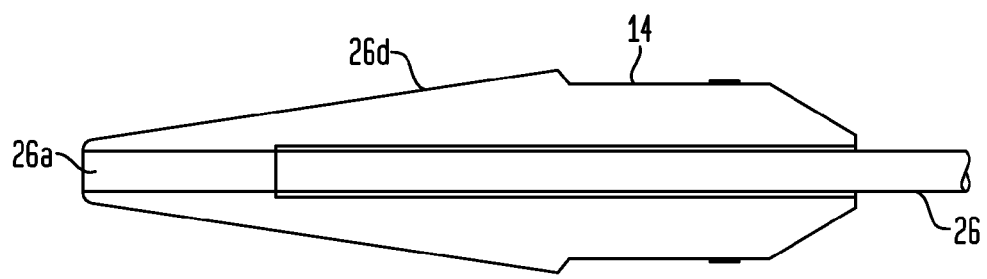
FIG. 12A is a longitudinal cross-section of one embodiment of an atraumatic tip.

Many modifications to the various features of the delivery devices described herein are possible. For example, modifications may be made to the atraumatic tip 14 of the catheter assembly 16. FIG. 12A shows a cross-section of the atraumatic tip 14 of FIG. 1A. The atraumatic tip 14 may have a lumen 26a extending longitudinally therethrough. The distal end of the inner shaft 26 may be inserted partially into the lumen 26a, and it may be held in place with an adhesive, ultrasonic welding, or other technique.

Figure 12B:
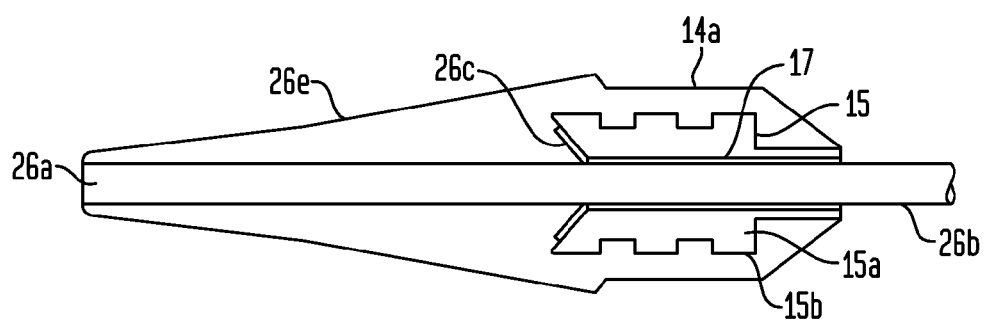
FIG. 12B is a longitudinal cross-section of an alternative embodiment of an atraumatic tip.

FIG. 12B shows a cross-section of an atraumatic tip 14a according to an alternate embodiment. An insert 15 may be assembled to the distal end of the inner shaft 26b. The insert 15 may have a plurality of ribs 15a that extend continuously or discontinuously around the circumference of the insert. The use of the insert 15 provides a strong connection between the tip 14 and the inner shaft 26b, and such use enables the inner shaft to extend by a lesser amount into the tip, such that the tip may be flexible along a greater extent of its length.

There are many ways that the atraumatic tip 14a, the insert 15, and the inner shaft 26b may be assembled with one another. In a preferred arrangement, the inner shaft 26b has a flared portion 26c at its distal end. The diameter of this flared portion preferably is greater than the diameter of a lumen 17 through the insert 15. The insert 15 may be assembled over the proximal end of the inner shaft 26b and slid distally until it contacts the flared portion 26c. Then, the atraumatic tip 14a may be molded around the insert 15 and the distal end of the inner shaft 26b, thereby locking the insert in place. As a result, the inner shaft 26b is prevented from moving proximally by the interference between the flared portion 26c and the distal end of the insert 15, and it is prevented from moving distally by the tip material molded around the flared portion, thus providing a secure attachment of the tip to the inner shaft.

The atraumatic tips 14 and 14a may be tapered along their lengths. For example, the atraumatic tip 14 may have a straight tapered surface 26d, and the atraumatic tip 14a may have a concavely tapered surface 26e. The radius of curvature of the tapered surface 26e may be about 4.0 to about 5.0 inches, with a radius of curvature of about 4.292 inches being preferred.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for a collapsible prosthetic heart valve, the delivery device comprising:
   an operating handle, including:
   a housing defining a movement space therein;
   a carriage assembly moveable in a longitudinal direction within the movement space;
   a deployment actuator coupled to the housing and rotatable relative to the housing; and
   a coupling assembly rotationally fixed to the deployment actuator, the coupling assembly having an engaged position in which rotation of the deployment actuator moves the carriage assembly in the longitudinal direction, and a disengaged position in which rotation of the deployment actuator does not move the carriage assembly in the longitudinal direction; and a catheter assembly, including:
a first shaft around which a compartment is defined, the first shaft being operatively connected to the housing, the compartment being adapted to receive the valve in an assembled condition; and a distal sheath operatively connected to the carriage assembly, the distal sheath being moveable between a closed condition covering the compartment and an open condition uncovering the compartment for deployment of the valve, wherein movement of the carriage assembly in the longitudinal direction in the movement space moves the distal sheath between the closed condition and the open condition, wherein the carriage assembly includes a threaded rod extending from a body of the carriage assembly and into threaded engagement with the coupling assembly, and wherein the coupling assembly includes a split nut having a plurality of threaded split nut portions, the split nut having an engaged position in which threads of the split nut portions are engaged with the threaded rod and a disengaged position in which the threads of the split nut portions do not engage the threaded rod.

2. The delivery device of claim 1, wherein rotation of the deployment actuator in a first direction moves the carriage assembly proximally in the longitudinal direction in the movement space, and rotation of the deployment actuator in a second direction opposite the first direction moves the carriage assembly distally in the longitudinal direction in the movement space.

3. The delivery device of claim 1, wherein the split nut portions each are linearly slideable away from one another and away from the threaded rod.

4. The delivery device of claim 3, wherein the coupling assembly includes a ring coupled to the split nut portions, the ring having cam surfaces, the split nut portions being slideable along the cam surfaces when the split nut portions move between the engaged and disengaged positions.

5. The delivery device of claim 1, wherein the deployment actuator is a knob rotatable about a central axis that extends parallel to the longitudinal direction.

6. The delivery device of claim 1, wherein the carriage assembly includes a toothed rack extending from a body of the carriage assembly and into threaded engagement with the coupling assembly.

7. The delivery device of claim 1, wherein the deployment actuator is a knob rotatable about a central axis that extends perpendicular to the longitudinal direction.

8. The delivery device of claim 1, wherein the operating handle further includes a resheathing lock having a lock position and a release position, the resheathing lock in the lock position limiting movement of the carriage assembly in the longitudinal direction to a stop position in the movement space, and the resheathing lock in the release position permitting movement of the carriage assembly beyond the stop position.

9. The delivery device of claim 8, wherein movement of the carriage assembly to the stop position moves the distal sheath to a condition between the closed condition and the open condition so that the valve is not fully deployed.

10. The delivery device of claim 8, wherein the compartment has a first length and the stop position in the movement space corresponds to a travel distance of the carriage assembly, the travel distance being less than the first length.

11. The delivery device of claim 10, wherein the collapsible prosthetic heart valve has a second length, and wherein the travel distance is between about 80% and about 90% of the second length.

12. The delivery device of claim 1, wherein the catheter assembly further includes an outer shaft attached to the distal sheath and operatively connected to the carriage assembly, the outer shaft at least partially surrounding the first shaft.

13. The delivery device of claim 1, wherein the operating handle further includes a mechanism adapted to move the first shaft proximally relative to the housing.

14. The delivery device of claim 1, wherein the first shaft is attached to the distal sheath and operatively connected to the carriage assembly, the catheter assembly further including an outer shaft connecting the housing to the compartment and at least partially surrounding the first shaft.

15. The delivery device of claim 1, wherein the catheter assembly further includes an atraumatic tip having a lumen extending longitudinally therethrough and an insert located within the lumen, the first shaft having an outwardly flared distal end that is fixed between a distal end of the insert and material forming the atraumatic tip.

16. The delivery device of claim 15, wherein the insert has a plurality of ribs, each rib extending continuously or discontinuously around a circumference of the insert.

17. The delivery device of claim 15, wherein the atraumatic tip has an outer surface that is concavely tapered in a longitudinal direction thereof.

18. A method of delivering a collapsible prosthetic heart valve in a patient, the method comprising:
providing a delivery device having a catheter assembly and an operating handle, the catheter assembly including a compartment adapted to receive the valve in an assembled condition, the operating handle including a housing defining a movement space therein, a carriage assembly moveable in first and second longitudinal directions within the movement space, a deployment actuator coupled to the housing and rotatable relative to the housing, and a coupling assembly rotationally fixed to the deployment actuator, the operating handle further including a threaded rod extending from the carriage assembly and into threaded engagement with the coupling assembly, the coupling assembly including a split nut having a plurality of threaded split nut portions, the split nut having an engaged position in which threads of the split nut portions are engaged with the threaded rod and a disengaged position in which the threads of the split nut portions do not engage the threaded rod;

loading the valve into the compartment of the catheter assembly and covering the compartment and the valve with a distal sheath of the catheter assembly;

inserting the catheter assembly into the patient so that the valve is positioned at a target location within the patient;

partially deploying the valve by moving the carriage assembly of the operating handle in the first longitudinal direction along a first portion of the movement space; and fully deploying the valve by continuing movement of the carriage assembly in the first longitudinal direction along a second portion of the movement space.

19. The method of claim 18, wherein the deployment actuator is longitudinally constrained relative to the housing, and the partially deploying step includes rotating the deployment actuator.

20. The method of claim 19, wherein the split nut portions each are linearly slideable away from one another and away from the threaded rod, the method further comprising moving the split nut portions from the disengaged position to the engaged position.

21. The method of claim 20, wherein the coupling assembly includes a ring coupled to the split nut portions, the ring having cam surfaces, and the step of moving the split nut portions includes sliding the split nut portions along the cam surfaces from the disengaged position to the engaged position.

22. The method of claim 19, wherein the deployment actuator is a knob rotatable about a central axis that extends parallel to the first and second longitudinal directions.

23. The method of claim 18, wherein the operating handle further includes a toothed rack extending from the carriage assembly and into engagement with the coupling assembly, the deployment actuator being longitudinally constrained relative to the housing, and the partially deploying step includes rotating the deployment actuator.

24. The method of claim 23, wherein the deployment actuator is a knob rotatable about a central axis that extends perpendicular to the first and second longitudinal directions.

25. The method of claim 18, wherein the catheter assembly further includes a first shaft around which the compartment is defined and an outer shaft connecting the carriage assembly to the distal sheath and at least partially surrounding the first shaft, the first shaft is fixedly connected to the housing, the distal sheath is operatively connected to the carriage assembly, and the steps of partially deploying the valve and fully deploying the valve each include moving the outer shaft proximally relative to the housing.

26. The method of claim 18, wherein the catheter assembly further includes a first shaft around which the compartment is defined and an outer shaft connecting the housing to the compartment and at least partially surrounding the first shaft, the first shaft and the distal sheath are operatively connected to the carriage assembly, and the steps of partially deploying the valve and fully deploying the valve each include moving the first shaft distally relative to the housing.

27. The method of claim 18, wherein the operating handle further includes a resheathing lock having a lock position and a release position, the resheathing lock in the lock position limiting movement of the carriage assembly in the first longitudinal direction to a stop position in the movement space, and the resheathing lock in the release position permitting movement of the carriage assembly in the first longitudinal direction beyond the stop position.

28. The method of claim 18, further comprising resheathing the valve by moving the carriage assembly in the second longitudinal direction opposite the first longitudinal direction.

29. The method of claim 18, wherein the target location is the native aortic annulus of the patient.

30. The method of claim 18, wherein the inserting step includes inserting the distal sheath of the catheter assembly through a femoral artery of the patient.

31. The method of claim 18, wherein the inserting step includes inserting the distal sheath of the catheter assembly through the apex of the heart of the patient.

32. A delivery device for a collapsible prosthetic heart valve, the delivery device comprising:
a first shaft around which a compartment is defined, the first shaft extending in a longitudinal direction and having an outwardly flared portion at a distal end thereof, the compartment being adapted to receive the valve in an assembled condition;
an outer shaft surrounding at least a longitudinal portion of the first shaft, the outer shaft being slidable relative to the first shaft in the longitudinal direction;
a distal sheath attached to one of the first shaft and the outer shaft and surrounding a longitudinal portion of the first shaft, the distal sheath being moveable in the longitudinal direction between a closed condition covering the compartment and an open condition uncovering the compartment for deployment of the valve, the distal sheath being operatively connected to a carriage assembly; and
an atraumatic tip attached to the distal end of the first shaft, the atraumatic tip having a lumen extending longitudinally therethrough and an insert located within the lumen, the outwardly flared portion of the first shaft being fixed between a distal end of the insert and material forming the atraumatic tip,
wherein the carriage assembly is moveable in first and second opposite directions and includes a threaded rod extending from the carriage assembly and into threaded engagement with a coupling assembly, the coupling assembly including a split nut having a plurality of threaded split nut portions, the split nut having an engaged position in which threads of the split nut portions are engaged with the threaded rod and a disengaged position in which the threads of the split nut portions do not engage the threaded rod.

33. The delivery device of claim 32, wherein the insert has a plurality of ribs, each rib extending continuously or discontinuously around a circumference of the insert.

34. The delivery device of claim 32, wherein the atraumatic tip has an outer surface that is concavely tapered in the longitudinal direction.

* * * * *